US011986553B2

(12) United States Patent
Yao et al.

(10) Patent No.: US 11,986,553 B2
(45) Date of Patent: May 21, 2024

(54) MULTI-COMPONENT INJECTION

(71) Applicant: TIANJIN CHASE SUN PHARMACEUTICAL CO. LTD, Wuqing Tianjin (CN)

(72) Inventors: Xiaoqing Yao, Wuqing Tianjin (CN); Changhai Sun, Wuqing Tianjin (CN); Kai Dong, Wuqing Tianjin (CN); Chuan Li, Wuqing Tianjin (CN); Guiping Zhang, Wuqing Tianjin (CN); Tianhao Dong, Wuqing Tianjin (CN); Jing Cao, Wuqing Tianjin (CN); Qiyun Wang, Wuqing Tianjin (CN); Xianjun Li, Wuqing Tianjin (CN); Junmin Gao, Wuqing Tianjin (CN); Mingzhen Sun, Wuqing Tianjin (CN)

(73) Assignee: TIANJIN CHASE SUN PHARMACEUTICAL CO. LTD, Waging Tianjin (CN)

( * ) Notice: Subject to any disclaimer, the term of this patent is extended or adjusted under 35 U.S.C. 154(b) by 377 days.

(21) Appl. No.: 17/235,126

(22) Filed: Apr. 20, 2021

(65) Prior Publication Data
US 2021/0346281 A1 Nov. 11, 2021

Related U.S. Application Data

(62) Division of application No. 15/737,808, filed as application No. PCT/CN2017/089695 on Jun. 23, 2017.

(30) Foreign Application Priority Data

Dec. 28, 2016 (CN) .......................... 201611232221.7

(51) Int. Cl.
| | | |
|---|---|---|
| A61K 9/00 | (2006.01) | |
| A61K 9/08 | (2006.01) | |
| A61K 31/192 | (2006.01) | |
| A61K 31/194 | (2006.01) | |
| A61K 31/198 | (2006.01) | |
| A61K 31/235 | (2006.01) | |
| A61K 31/343 | (2006.01) | |
| A61K 31/353 | (2006.01) | |
| A61K 31/513 | (2006.01) | |
| A61K 31/52 | (2006.01) | |
| A61K 31/7048 | (2006.01) | |
| A61K 31/7064 | (2006.01) | |
| A61K 31/7076 | (2006.01) | |
| A61K 31/708 | (2006.01) | |
| A61K 36/232 | (2006.01) | |
| A61K 36/236 | (2006.01) | |
| A61K 36/28 | (2006.01) | |

(Continued)

(52) U.S. Cl.
CPC .............. *A61K 9/0019* (2013.01); *A61K 9/08* (2013.01); *A61K 31/192* (2013.01); *A61K 31/194* (2013.01); *A61K 31/198* (2013.01); *A61K 31/235* (2013.01); *A61K 31/343* (2013.01); *A61K 31/353* (2013.01); *A61K 31/513* (2013.01); *A61K 31/52* (2013.01); *A61K 31/7048* (2013.01); *A61K 31/7064* (2013.01); *A61K 31/7076* (2013.01); *A61K 31/708* (2013.01); *A61K 36/232* (2013.01); *A61K 36/236* (2013.01); *A61K 36/28* (2013.01); *A61K 36/286* (2013.01); *A61K 36/537* (2013.01); *A61K 36/65* (2013.01); *A61K 47/26* (2013.01); *A61P 31/04* (2018.01); *A61K 2236/331* (2013.01); *A61K 2236/333* (2013.01); *A61K 2236/37* (2013.01); *A61K 2236/39* (2013.01); *A61K 2236/53* (2013.01)

(58) Field of Classification Search
CPC ...... A61K 9/0019; A61K 9/08; A61K 31/192; A61K 31/194; A61K 31/198; A61K 31/235; A61K 31/343; A61K 31/353; A61K 31/513; A61K 31/52; A61K 31/7048; A61K 31/7064; A61K 31/7076; A61K 31/708; A61K 36/232; A61K 36/236; A61K 36/28; A61K 36/286; A61K 36/537; A61K 36/65; A61K 47/26; A61K 2236/331; A61K 2236/333; A61K 2236/37; A61K 2236/39; A61K 2236/53; A61P 31/04

See application file for complete search history.

(56) References Cited

U.S. PATENT DOCUMENTS

2019/0269609 A1 9/2019 Yao et al.

FOREIGN PATENT DOCUMENTS

| CN | 1432391 A | 7/2003 |
|---|---|---|
| CN | 1190223 C * | 2/2005 |

(Continued)

OTHER PUBLICATIONS

Li HM, Zheng YF, Zhi XL, Li CY, Jiang Y, Peng GP "Comparison of activated carbon and ultrafiltration technique in the production process of huoxue tongluo injection" Zhong Yao Cai, Dec. 2012, 35(12), pp. 2012-2015; PMID 23705368. (Year: 2012).*

(Continued)

*Primary Examiner* — Aaron J Kosar
(74) *Attorney, Agent, or Firm* — Finnegan, Henderson, Farabow, Garrett & Dunner, LLP

(57) ABSTRACT

The invention relates to the technical field of medicines, and particularly relates to a multi-component injection and preparation processes and applications thereof. In the present invention, the effective ingredients of safflower *Carthamus*, Red Paeony Root, *Ligusticum wallichii*, *Radix salvia miltiorrhizae* and *Angelica sinensis* are analyzed and a multi-component injection is prepared via the modem pharmaceutical preparation technology. The study proves that the multi-component injection of the invention has therapeutic effects on Sepsis.

11 Claims, 2 Drawing Sheets

Figure 1:
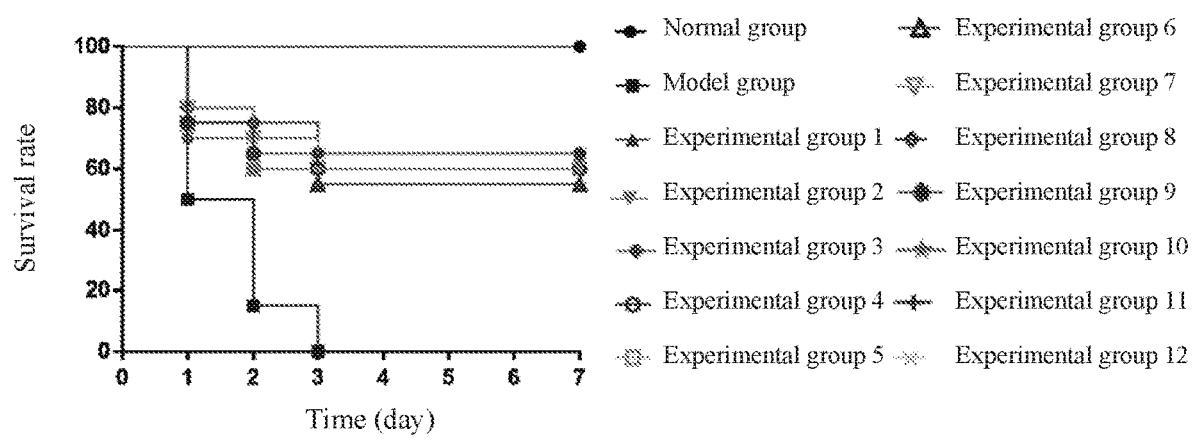

(51) Int. Cl.
A61K 36/286 (2006.01)
A61K 36/537 (2006.01)
A61K 36/65 (2006.01)
A61K 47/26 (2006.01)
A61P 31/04 (2006.01)

(56) References Cited

FOREIGN PATENT DOCUMENTS

| CN | 101683318 A | * | 3/2010 |
|---|---|---|---|
| CN | 104297375 A | | 1/2015 |
| CN | 106727649 A | | 5/2017 |

OTHER PUBLICATIONS

Shang T, et al "Xuebijing Injection Maintains GRP78 Expression to Prevent Candida albicans-Induced Epithelial Death in the Kidney" Front. Pharmacol., Jan. 6, 2020, 10, No. 1416, 14 pages; doi: 10.3389/fphar.2019.01416. (Year: 2020).*
Zhang L, et al "Beneficial effect of Xuebijing against Pseudomonas aeruginosa infection in Caenorhabditis elegans" Front Pharmacol, 2022 (ePub Aug. 31, 2022), 13: 949608, 12 pages (PMID 36120363); doi: 10.3389/fphar.2022.949608. (Year: 2022).*
Ai, Yu-Hang et al., "Effect of apoptosis of $CD_4^+$ CD25+ regulatory T cells on proliferation as well as secretion of effector T cells and interventional activity of Xuebijing injection in septicrats," *Chin J Surg.*, vol. 47, No. 1 pp. 58-61 (Jan. 2009).
Mathias, Brittany et al., "A Review of GM-CSF Therapy in Sepsis," Medicine vol. 94 No. 50, pp. 1-10 (Dec. 2015).
Chen, Yunxia et al., "The effectiveness of XueBiJing injection in therapy of sepsis: a multicenter clinical study," Chin J Emerg Med, vol. 22, No. 2 pp. 130-135 (Feb. 2013).
Gao, Jie et al., "A prospective multicenter clinical study ofXuebijing injection in the treatment of sepsis and multiple organ dysfunction syndrome," Chinese Critical Care Med., vol. 27, No. 6 pp. 465-470 (Jun. 2015).
Gui, Yong-Gang et al., "Effects of Xuebijing injection on tissue factor of monocytes and coagulation parameters in septic rats," Chin J Exp Surg, vol. 27, No. 1 pp. 32-34 (Jan. 2010).
Hu, Jing et al., "Xuebijing injection for sepsis: a comprehensive review," Medical Journal of Chinese People's Liberation Army, vol. 35, No. 1 pp. 9-12 (Jan. 2010).
Gotts, Jeffrey E., et al., "Sepsis: pathophysiology and clinical management," The BMJ, pp. 365-378 (May 2016).
Ye, Jin, Research on the process of removing tannin from Radix Paeoniae Rubra injection, Chinese Traditional Patent Medicine, vol. 28, No. 10 pp. 1524-1526 (Oct. 2006).

Wang, Jinda et al., Sepsis treatment from "three kinds of Traditional Chinese Medicine (TCM) syndromes and three kinds of Chinese herbal medicine therapies," Chin Crit Care Med, vol. 18, No. 11 pp. 643-644 (Nov. 2006).
Li, Xin et al. "Effect of Xuebijing injection on expression of tissue factor in renal micro-vascular endothelial cells induced by lipopolysaccharide and the possible mechanisms," Chinese J TCM WM Critical Care, vol. 16, No. 4 pp. 218-223 (Jul. 2009).
Wang, Liang et al., "Effects of Xuebijing injection on microcirculation in septic shock," Journal of Surgical Research vol. 202, pp. 147-154 (2016).
Gentile, Lori F. et al., "Persistent inflammation and immunosuppression: A common syndrome and new horizon for surgical intensive care," J Trauma Acute Care Surg., vol. 75, No. 6 pp. 1-18 (Jun. 2012).
Singer, M. et al., "The Third International Consensus Definitions for Sepsis and Septic Shock (Sepsis-3)," JAMA vol. 315, No. 8 pp. 801-810 (Feb. 2015).
Dellinger, R. Phillip et al., "Surviving Sepsis Campaign: International Guidelines for Management of Severe Sepsis and Septic Shock: 2012," Critical Care Medicine vol. 41, No. 2 pp. 580-637 (Feb. 2013).
Wang, Qiao et al., "Xuebijing Ameliorates Sepsis-Induced Lung Injury by Down Regulating HMGB1 and Rage Expressions in Mice," Evidence-Based Complementary and Alternative Medicine vol. 2015, pp. 1-10 (2015).
Liu, Yan-Cu et al., "Xuebijing Injection Promotes M2 Polarization of Macrophages and Improve Survival Rate in Septic Mice," Evidence-Based Complementary and Alternative Medicine Vo. 2015, Article ID 352642 pp. 1-9 (2015).
Yao, Yong-Ming et al., "The Effect of a Novel Cytokine, High Mobility Group Box 1 Protein, on the Development of Traumatic Sepsis," Chinese Journal of Integrated Med., vol. 15 No. 1, pp. 13-15 (Feb. 2009.
Li, Zhijun, Research progress on sepsis treatmentwith "three kinds of Traditional Chinese Medicine (TCM) syndromes and three kinds of Chinese herbal medicine therapies" and "combined treatment with bacteriovitis," Chinese Journal of Surgery of Integrated Traditional and Western Medicine, 2012, 18 (6) 553-554.
Tierra, M."Remove Blood Stagnation in the Chest Decoction" from "Chinese Traditional Herbal Medicine vol. 1". Lotus Press: WI. 19981 page. (Year: 1998).
Li, Hui-qin et al. "Promoting blood circulation for removing blood stasis therapy for acute intracerebral hemorrhage: a systematic review and meta-analysis," *Acta Pharmacologica Sinica* vol. 36, pp. 659-675 (2015).
International Search Report and Written Opinion of the International Search Authority in PCT/CN2017/089695 (English translation included), Sep. 21, 2017, 16 pages.

* cited by examiner

MULTI-COMPONENT INJECTION

This application is a divisional application of U.S. application Ser. No. 15/737,808, filed Dec. 19, 2017, which is a national stage filing under 35 U.S.C. § 371 of International Application No. PCT/CN2017/089695, filed Jun. 23, 2017, which claims priority of Chinese Patent Application No. 201611232221.7, filed Dec. 28, 2016. The contents of these applications are each incorporated herein by reference.

I. TECHNICAL FIELD

The present invention relates to the technical field of medical technology, and particularly relates to a multi-component injection and preparation processes and applications thereof.

II. BACKGROUND OF THE INVENTION

Sepsis is a fatal organ dysfunction caused by the reaction disorder of the infected hosts, with a hospital mortality of more than 10%, which has posed a huge threat to human health, becoming a focus to which the medical field pays close attention [see JAMA. 2016 Feb. 23; 315(8):801-10]. Under the big data retrospective analysis in combination with the microarray technology and analysis of leukocyte gene expression, people gradually realize that Sepsis is not only a process of systemic inflammatory reaction or immune disorder, but also a complex chronic critical disease combining sustained inflammation, immunosuppression and catabolism. [See J Trauma Acute Care Surg. 2012 June; 72(6): 1491-501, BMJ. 2016 May 23; 353: i1585 and Medicine (Baltimore). 2015 Dee; 94(50):e2044.].

For many years, antibiotics, antiviral medicines, vasopressor medicines, etc. are used for the traditional treatment of Sepsis. However, there are not enough specific medicines put into clinical practice aiming at the pathogenesis of Sepsis. [See Crit Care Med. 2013 February; 41(2):580-637]. How to timely correct the systemic inflammatory reaction, coagulation disorders and immune dysfunction in the development process of Sepsis, restore proinflammatory-antiinflammatory dynamic balance of organisms as early as possible, and effectively improve the prognosis of patients have become the important issues to be solved in the research and development of Sepsis treatment medicines.

In 1970s, Professor Jinda Wang, a Chinese famous first-aid medical expert, presented the rules of treatment by traditional Chinese medicine for treating acute and critical diseases: the method of heat-clearing and detoxicating remedy is used for treating toxic-heat syndrome, the method for promoting blood circulation and removing blood-stasis is used for treating syndrome of blood stasis, and the method for supporting the healthy energy is used for treating acute asthenic symptoms, i.e., "Three Syndromes and Three Methods", which are used as the basic methods of clinical practice for treating Sepsis [See China first-aid medicine of critical diseases, 2006, 18 (11): 643-4]. In 1975, he firstly confirmed that endotoxemia was the initial etiology of infectious multiple system organ failure, and proposed a new treatment strategy of "Treatment for both germs andendotoxin". As he realized that the harm of endotoxin to organisms included inducing the production of in-vivo inflammatory media and then showing toxic effects, he further proposed treatment for bacteria, endotoxin and inflammatory media together, i.e., "Treatment for bacteria, endotoxin and inflammatory media together" [See Chinese Journal of Surgery of Integrated Traditional and Western Medicine, 2012, 18 (6): 553-554].

"Xuebijing injection" is an intravenous injection developed on the basis of "Xuefu Zhuyu Decoction" recorded in Wang Qingren's "Corrections on the Errors of Medical Works" in Qing Dynasty in accordance with the syndrome differentiation principle of "Three Syndromes and Three Methods" under the theoretical guidance of "Treatment for bacteria, endotoxin and inflammatory media together". The "Xuebijing injection" is prepared from five medicinal materials, i.e., safflower (Carthamus tinctorius), Red Paeony Root, Ligusticum wallichii, Radix salviae miltiorrhizae and Chinese angelica (Angelica sinensis), via extraction, refining, drying, blending and other modern techniques. The "Xuebijing injection" belongs to the traditional Chinese medicine for dispersing blood stasis and detoxifying, which is applied for warm heat diseases, such as fever, dyspnea, tachypnea, palpitation, dysphoria and other syndromes of intermingling of blood statsis and toxin, and is suitable for the systemic inflammatory reaction syndrome induced by infection. The Xuebijing injection can also be used during the period of organ function lesion for treatment of multi-organ disfunction syndrome. The "Xuebijing injection" has the pharmacological actions of antagonizing bacterial endotoxin [See Chinese critical care medicine, 2006, 18 (11): 643-4], inhibiting inflammatory factors from being released excessively [See Chinese critical care medicine, 2006, 18 (11): 643-4, Evid Based Complement Alternat Med. 2015; 2015:860259 and Chin J Integr Med. 2009; 15(1): 13-5], overcoming coagulation disorders [See Chinese Journal of Experimental Surgery, 2010, 27 (1): 32-4 and Chinese Journal of Integrated traditional and Western Medicine in Critical Care, 2009, 16 (4): 218-22], protecting vascular endothelial cells [See Chinese Journal of Integrated traditional and Western Medicine in Critical Care, 2009, 16 (4): 218-221, improving the microcirculation of tissue [See J Surg Res. 2016 May 1; 202(1):147-54], and improving immune dysfunction [see Chinese Journal of Surgery, 2009, 47 (1): 58-61 and Evid Based Complement Alternat Med. 2015; 2015:352642], which fully embodies the integrated regulatory effects of having multiple components, multiple links, multiple channels and multiple target points of traditional Chinese medicine. The results of the multi-centric clinical study with large sample sizes and meta analysis (Meta) indicate that it can reduce the 28d case fatality rate and incidence rate of complication of Sepsis patients, shorten the average hospital stay, effectively improve the clinical indexes including systemic inflammatory response, coagulation function of patients, and the scoring of the scoring system II for acute physiology and chronic health condition (APACHE II), protect organ function, and significantly improve the clinical effect on the basis of the conventional comprehensive treatment in combination with the use of the "Xuebijing injection" [See Chinese critical care medicine 2015, 27(6): 465-76, Chinese Journal of Emergency Medicine, 2013, 22 (2): 130-5 and Medical Journal of Chinese People's Liberation Army, 2010, 35 (1): 9-12].

In 2003, Chinese patent 03104977.X disclosed "a Chinese medicinal preparation for treating Sepsis and a preparation method thereof", i.e., a preparation method for the "Xuebijing injection", and its preparation process has been very matured. With the progress and innovation of science and technology, we carry out optimization on the process and elaboration of technological parameters, i.e., changing the removal of the heat source by 1% activated carbon in the original preparation process into ultrafiltration, thereby ensuring the safety of finished products and uniform and stable quality. The inventors, by means of the advanced research concept and instrument and equipment, have achieved the full-ingredient testing of such injection. We acquire a brand-new multi-component injection via the study on the material basis of the Xuebijing injection, in which the effective ingredients of the original "Xuebijing injection" are preserved.

III. SUMMARY OF THE INVENTION

The invention provides a multi-component injection, which is characterized by comprising the following active ingredients, by weight: 8.66-35.26 parts of albiflorin std, 1000.0-1700.0 parts of paeoniflorin, 11.13-68.07 parts of Oxypaeoniflorin, 12.20-52.98 parts of Benzoylpaeoniflorin, 0.667-1.617 parts of Benzoyloxypaeoniflorin, 1.915-3.202 parts of Mudanpioside J, 10.63-20.13 parts of galloylpaeoniflorin, 0.804-1.338 parts of Mudanpioside C, 10.0-200.0 parts of benzoic acid, 0.21-15.88 parts of gallic acid, 0.2396-0.6860 parts of ethyl gallate, and 1.31-12.60 parts of catechin.

The above-mentioned multi-component injection is characterized in that the preparation method thereof comprises the following steps:
  providing 100 g of Red Paeony Root decoction pieces; heating and boiling the Red Paeony Root decoction pieces with process water of 10 times the weight of the Red Paeony Root decoction pieces to obtain a first decoction after 2 hours slight boiling; filtering the first decoction to obtain filtrate I and a first dreg; boiling the first dreg with process water of 8 times the weight of the first dreg to obtain a second decoction after 1 hour slight boiling; filtering the second decoction to obtain filtrate II and a second dreg; mixing filtrate I and filtrate II to obtain a mixture; concentrating the mixture to obtain a first concentrate of 100 ml; adding a proper amount of gelatin solution to the first concentrate under stirring to obtain a gelatin-containing first concentrate; adding 95% ethanol to the gelatin-containing first concentrate to obtain an ethanol-containing first concentrate having an ethanol volume content of 70%; storing the ethanol-containing first concentrate under cooling condition for 24 hours to obtain a cool ethanol-containing first concentrate; filtering and concentrating the cool ethanol-containing first concentrate to obtain a second concentrate of 100 ml; extracting the second concentrate with water-saturated n-butanol for 4 times and using water-saturated n-butanol of 50 ml for each time; combining extract liquors of the 4 times extraction to obtain a combined extract liquor; recycling n-butanol from the combined extract liquor to obtain a n-butanol-reduced extract liquor without alcohol taste; and vacuum drying the n-butanol-reduced extract liquor to obtain a Red Paeony Root dry paste;
  providing a proper amount of the Red Paeony Root dry paste; dissolving the Red Paeony Root dry paste in injection water to obtain a dilute of 200 ml; storing the dilute under cooling condition to obtain a first cool liquid; adding glucosum anhydricum of an amount in accordance with 4.5% mass fraction of the multi-component injection and injection water to the first cool liquid to obtain a 1000 ml liquid; adjusting the pH value of the 1000 ml liquid to 5.5-7.0 with a sodium hydroxide solution of 10% mass fraction to obtain a pH adjusted liquid; storing the pH adjusted liquid under cooling condition to obtain a second cool liquid; subjecting the second cool liquid to ultrafiltration to obtain an ultrafiltrate; adding a proper amount of solubilizing auxiliary materials which are dissolved in a proper amount of injection water into the ultrafiltrate to obtain a solubilizing auxiliary materials-containing ultrafiltrate; adjusting the pH value of the solubilizing auxiliary materials-containing ultrafiltrate to 5.5-7.0 using the sodium hydroxide solution of 10% mass fraction to obtain a pH adjusted ultrafiltrate; filtering the pH adjusted ultrafiltrate to obtain a filtrate; encapsulating and sterilizing the filtrate to obtain the multi-component injection.

On the basis of the above-mentioned multi-component injection, the present invention further provides a multi-component injection, which is characterized by comprising the following active ingredients, by weight: 8.66-35.26 parts of albiflorin std, 1000.0-1700.0 parts of paeoniflorin, 11.13-68.07 parts of Oxypaeoniflorin, 12.20-52.98 parts of Benzoylpaeoniflorin, 0.667-1.617 parts of Benzoyloxypaeoniflorin, 1.915-3.202 parts of Mudanpioside J, 10.63-20.13 parts of galloylpaeoniflorin, 0.804-1.338 parts of Mudanpioside C, 10.0-200.0 parts of benzoic acid, 0.21-15.88 parts of gallic acid, 0.2396-0.6860 parts of ethyl gallate, 1.31-12.60 parts of catechin, 1.232-3.547 parts of Kaempferol-3-0-glucoside, 0.0500-0.4184 parts of scutellarin, 0.755-2.570 parts of quercetin-3-0-glucoside, 8.42-29.40 parts of Kaempferol-3-0-rutinoside, 4.036-7.695 parts of Kaempferol-3-0-sophoroside, 1.517-5.598 parts of quercetin-3-0-rutinoside, 200.0-500.0 parts of Hydroxysafflor yellow A, 0.316-0.774 parts of uracil, 13.77-30.56 parts of adenine, 20.50-44.99 parts of phenylalanine, 11.44-27.13 parts of uridine, 5.07-12.63 parts of adenosine, 8.00-24.11 parts of guanosine, 4.96-16.86 parts of butanedioic acid, 2.384-5.404 parts of p-hydroxybenzoic acid, 3.00-17.98 parts of p-coumaric acid, 4.837-7.806 parts of caffeic acid and 3.83-8.59 parts of chlorogenic acid.

The above-mentioned multi-component injection is characterized in that the preparation method thereof comprises the following steps:
  providing 100 g of safflower (*Carthamus tinctorius*) decoction pieces; leaching the safflower decoction pieces with 30% ethanol of 8 times the weight of the safflower decoction pieces for 8 hours to obtain a leach liquor; filtering the leach liquor to obtain a liquid medicine of 4-6 times the weight of the safflower decoction pieces; adding 95% ethanol to the liquid medicine to obtain an ethanol-containing liquid medicine having an ethanol volume content of 70%; storing the ethanol-containing liquid medicine under cooling condition for 48 hours to obtain a cool ethanol-containing liquid medicine; filtering the cool ethanol-containing liquid medicine to obtain a first filtrate; concentrating the first filtrate under reduced pressure to obtain a concentrate of 100 ml; adding 95% ethanol to the concentrate to obtain an ethanol-containing concentrate having an ethanol volume content of 80%; storing the ethanol-containing concentrate under cooling condition for 48 hours to obtain a cool ethanol-containing concentrate; filtering the cool ethanol-containing concentrate to obtain a second filtrate; recycling ethanol from the second filtrate to obtain an ethanol-reduced filtrate; concentrating and vacuum drying the ethanol-reduced filtrate to obtain a safflower dry paste;
  providing 100 g of Red Paeony Root decoction pieces; heating and boiling the Red Paeony Root decoction pieces with process water of 10 times the weight of the Red Paeony Root decoction pieces to obtain a first decoction after 2 hours slight boiling; filtering the first decoction to obtain filtrate I and a first dreg; boiling the first dreg with process water of 8 times the weight of the first dreg to obtain a second decoction after 1 hour slight boiling; filtering the second decoction to obtain filtrate II and a second dreg; mixing filtrate I and filtrate II to obtain a mixture; concentrating the mixture to obtain a first concentrate of 100 ml; adding a proper amount of gelatin solution to the first concentrate under stirring to obtain a gelatin-containing first concentrate; adding 95% ethanol to the gelatin-containing first concentrate to obtain an ethanol-containing first concentrate having an ethanol volume content of 70%; storing the ethanol-containing first concentrate under cooling condition for 24 hours to obtain a cool ethanol-containing first concentrate; filtering and concentrating the cool ethanol-containing first concentrate to obtain a second concentrate of 100 ml; extracting the second concentrate with water-saturated n-butanol for 4 times and using 50 ml water-saturated n-butanol for each time; combining extract liquors of the 4 times extraction to obtain a combined extract liquor; recycling n-butanol from the combined extract liquor to obtain a n-butanol-reduced extract liquor without alcohol taste; and vacuum drying the n-butanol-reduced extract liquor to obtain a Red Paeony Root dry paste;

providing the safflower dry paste and the Red Paeony Root dry paste each of a proper amount; dissolving the two dry pastes in injection water to obtain a dilute of 200 ml; storing the dilute under cooling condition to obtain a first cool liquid; adding glucosum anhydricum of an amount in accordance with 4.5% mass fraction of the multi-component injection and injection water to the first cool liquid to obtain a 1000 ml liquid; adjusting the pH value of the 1000 ml liquid to 5.5-7.0 with a sodium hydroxide solution of 10% mass fraction to obtain a pH adjusted liquid; storing the pH adjusted liquid under cooling condition to obtain a second cool liquid; subjecting the second cool liquid to ultrafiltration to obtain an ultrafiltrate; adding a proper amount of solubilizing auxiliary materials which are dissolved in a proper amount of injection water into the ultrafiltrate to obtain a solubilizing auxiliary materials-containing ultrafiltrate; adjusting the pH value of the solubilizing auxiliary materials-containing ultrafiltrate to 5.5-7.0 using the sodium hydroxide solution of 10% mass fraction to obtain a pH adjusted ultrafiltrate; filtering the pH adjusted ultrafiltrate to obtain a filtrate; encapsulating and sterilizing the filtrate to obtain the multi-component injection.

On the basis of the above-mentioned multi-component injection, the present invention further provides a multi-component injection, which is characterized by comprising the following active ingredients, by weight: 8.66-35.26 parts of albiflorin std, 1000.0-1700.0 parts of paeoniflorin, 11.13-68.07 parts of Oxypaeoniflorin, 12.20-52.98 parts of Benzoylpaeoniflorin, 0.667-1.617 parts of Benzoyloxypaeoniflorin, 1.915-3.202 parts of Mudanpioside J, 10.63-20.13 parts of galloylpaeoniflorin, 0.804-1.338 parts of Mudanpioside C, 10.0-200.0 parts of benzoic acid, 0.21-15.88 parts of gallic acid, 0.2396-0.6860 parts of ethyl gallate, 1.31-12.60 parts of catechin, 1.232-3.547 parts of Kaempferol-3-0-glucoside, 0.0500-0.4184 parts of scutellarin, 0.755-2.570 parts of quercetin-3-0-glucoside, 8.42-29.40 parts of Kaempferol-3-0-rutinoside, 4.036-7.695 parts of Kaempferol-3-0-sophoroside, 1.517-5.598 parts of quercetin-3-0-rutinoside, 200.0-500.0 parts of Hydroxysafflor yellow A, 0.316-0.774 parts of uracil, 13.77-30.56 parts of adenine, 20.50-44.99 parts of phenylalanine, 11.44-27.13 parts of uridine, 5.07-12.63 parts of adenosine, 8.00-24.11 parts of guanosine, 4.96-16.86 parts of butanedioic acid, 2.384-5.404 parts of p-hydroxybenzoic acid, 3.00-17.98 parts of p-coumaric acid, 4.837-7.806 parts of caffeic acid, 3.83-8.59 parts of chlorogenic acid, 6.51-69.39 parts of senkyunolide I (42), 1.55-18.27 parts of senkyunolide H, 4.30-14.22 parts of senkyunolide N, 2.460-5.648 parts of open-loop senkyunolide I, 1.55-10.74 parts of senkyunolide G, 1.43-8.67 parts of 3-hydroxyl-3-butylphthalide, 0.10-0.961 parts of senkyunolide A, and 7.66-47.15 parts of ferulaic acid.

The above-mentioned multi-component injection is characterized in that the preparation method thereof comprises the following steps:

taking 100 g of *Ligusticum wallichii* and *Angelica sinensis* decoction pieces respectively, treating in accordance with the Red Paeony Root process, keeping 300 ml of concentrated solution every time, and extracting with 150 ml of water saturated normal butanol each time to prepare dry paste;

providing 100 g of safflower (*Carthamus tinctorius*) decoction pieces; leaching the safflower decoction pieces with 30% ethanol of 8 times the weight of the safflower decoction pieces for 8 hours to obtain a leach liquor; filtering the leach liquor to obtain a liquid medicine of 4-6 times the weight of the safflower decoction pieces; adding 95% ethanol to the liquid medicine to obtain an ethanol-containing liquid medicine having an ethanol volume content of 70%; storing the ethanol-containing liquid medicine under cooling condition for 48 hours to obtain a cool ethanol-containing liquid medicine; filtering the cool ethanol-containing liquid medicine to obtain a first filtrate; concentrating the first filtrate under reduced pressure to obtain a concentrate of 100 ml; adding 95% ethanol to the concentrate to obtain an ethanol-containing concentrate having an ethanol volume content of 80%; storing the ethanol-containing concentrate under cooling condition for 48 hours to obtain a cool ethanol-containing concentrate; filtering the cool ethanol-containing concentrate to obtain a second filtrate; recycling ethanol from the second filtrate to obtain an ethanol-reduced filtrate; concentrating and vacuum drying the ethanol-reduced filtrate to obtain a safflower dry paste;

providing 100 g of Red Paeony Root decoction pieces; heating and boiling the Red Paeony Root decoction pieces with process water of 10 times the weight of the Red Paeony Root decoction pieces to obtain a first decoction after 2 hours slight boiling; filtering the first decoction to obtain filtrate I and a first dreg; boiling the first dreg with process water of 8 times the weight of the first dreg to obtain a second decoction after 1 hour slight boiling; filtering the second decoction to obtain filtrate II and a second dreg; mixing filtrate I and filtrate II to obtain a mixture; concentrating the mixture to obtain a first concentrate of 100 ml; adding a proper amount of gelatin solution to the first concentrate under stirring to obtain a gelatin-containing first concentrate; adding 95% ethanol to the gelatin-containing first concentrate to obtain an ethanol-containing first concentrate having an ethanol volume content of 70%; storing the ethanol-containing first concentrate under cooling condition for 24 hours to obtain a cool ethanol-containing first concentrate; filtering and concentrating the cool ethanol-containing first concentrate to obtain a second concentrate of 100 ml; extracting the second concentrate with water-saturated n-butanol for 4 times and using 50 ml water-saturated n-butanol for each time; combining extract liquors of the 4 times extraction to obtain a combined extract liquor; recycling n-butanol from the combined extract liquor to obtain a n-butanol-reduced extract liquor without alcohol taste; and vacuum drying the n-butanol-reduced extract liquor to obtain a Red Paeony Root dry paste;

providing 100 g of *Ligusticum wallichii* decoction pieces and 100 g of *Angelica sinensis* decoction pieces; treating the *Ligusticum wallichii* decoction pieces and *Angelica sinensis* decoction pieces with a same treatment process as the Red Paeony Root decoction pieces except for keeping 300 ml of concentrate every time and extracting with 150 ml of water-saturated n-butanol each time, to obtain a third dry paste;

providing the safflower dry paste, the Red Paeony Root dry paste and the third dry paste each of a proper amount; dissolving the three dry pastes in injection water to obtain a dilute of 200 ml; storing the dilute under cooling condition to obtain a first cool liquid; adding glucosum anhydricum of an amount in accordance with 4.5% mass fraction of the multi-component injection and injection water to the first cool liquid to obtain a 1000 ml liquid; adjusting the pH value of the 1000 ml liquid to 5.5-7.0 with a sodium hydroxide solution of 10% mass fraction to obtain a pH adjusted liquid; storing the pH adjusted liquid under cooling condition to obtain a second cool liquid; subjecting the second cool liquid to ultrafiltration to obtain an ultrafiltrate; adding a proper amount of solubilizing auxiliary materials which are dissolved in a proper amount of injection water into the ultrafiltrate to obtain a solubilizing auxiliary materials-containing ultrafiltrate; adjusting the pH value of the solubilizing auxiliary materials-containing ultrafiltrate to 5.5-7.0 using the sodium hydroxide solution of 10% mass fraction to obtain a pH adjusted ultrafiltrate; filtering the pH adjusted ultrafiltrate to obtain a filtrate; encapsulating and sterilizing the filtrate to obtain the multi-component injection.

On the basis of the above-mentioned multi-component injections, the present invention further provides a multi-component injection, which is characterized by comprising the following active ingredients, by weight: 8.66-35.26 parts of albiflorin std, 1000.0-1700.0 parts of paeoniflorin, 11.13-68.07 parts of Oxypaeoniflorin, 12.20-52.98 parts of Benzoylpaeoniflorin, 0.667-1.617 parts of Benzoyloxypaeoniflorin, 1.915-3.202 parts of Mudanpioside J, 10.63-20.13 parts of galloylpaeoniflorin, 0.804-1.338 parts of Mudanpioside C, 10.0-200.0 parts of benzoic acid, 0.21-15.88 parts of gallic acid, 0.2396-0.6860 parts of ethyl gallate, 1.31-12.60 parts of catechin, 1.232-3.547 parts of Kaempferol-3-0-glucoside, 0.0500-0.4184 parts of scutellarin, 0.755-2.570 parts of quercetin-3-0-glucoside, 8.42-29.40 parts of Kaempferol-3-0-rutinoside, 4.036-7.695 parts of Kaempferol-3-0-sophoroside, 1.517-5.598 parts of quercetin-3-0-rutinoside, 200.0-500.0 parts of Hydroxysafflor yellow A, 0.316-0.774 parts of uracil, 13.77-30.56 parts of adenine, 20.50-44.99 parts of phenylalanine, 11.44-27.13 parts of uridine, 5.07-12.63 parts of adenosine, 8.00-24.11 parts of guanosine, 4.96-16.86 parts of butanedioic acid, 2.384-5.404 parts of p-hydroxybenzoic acid, 3.00-17.98 parts of p-coumaric acid, 4.837-7.806 parts of caffeic acid, 3.83-8.59 parts of chlorogenic acid, 6.51-69.39 parts of senkyunolide I (42), 1.55-18.27 parts of senkyunolide H, 4.30-14.22 parts of senkyunolide N, 2.460-5.648 parts of open-loop senkyunolide I, 1.55-10.74 parts of senkyunolide G, 1.43-8.67 parts of 3-hydroxyl-3-butylphthalide, 0.10-0.961 parts of senkyunolide A, 7.66-47.15 parts of ferulaic acid, 1.43-17.25 parts of protocatechualdehyde, 2.361-4.030 parts of protocatechuic acid, 2.776-6.845 parts of tanshinol, 5.07-12.78 parts of rosmarinic acid, 0.0697-0.4005 parts of salvianolic acid D, 1.123-4.732 parts of salvianolic acid C, 0.366-2.505 parts of salvianolic acid A, 0.429-0.945 parts of alkannic acid, and 4.00-11.00 parts of salvianolic acid B.

The above-mentioned multi-component injection is characterized in that the preparation method thereof comprises the following steps:

providing 100 g of safflower (*Carthamus tinctorius*) decoction pieces; leaching the safflower decoction pieces with 30% ethanol of 8 times the weight of the safflower decoction pieces for 8 hours to obtain a leach liquor; filtering the leach liquor to obtain a liquid medicine of 4-6 times the weight of the safflower decoction pieces; adding 95% ethanol to the liquid medicine to obtain an ethanol-containing liquid medicine having an ethanol volume content of 70%; storing the ethanol-containing liquid medicine under cooling condition for 48 hours to obtain a cool ethanol-containing liquid medicine; filtering the cool ethanol-containing liquid medicine to obtain a first filtrate; concentrating the first filtrate under reduced pressure to obtain a concentrate of 100 ml; adding 95% ethanol to the concentrate to obtain an ethanol-containing concentrate having an ethanol volume content of 80%; storing the ethanol-containing concentrate under cooling condition for 48 hours to obtain a cool ethanol-containing concentrate; filtering the cool ethanol-containing concentrate to obtain a second filtrate; recycling ethanol from the second filtrate to obtain an ethanol-reduced filtrate; concentrating and vacuum drying the ethanol-reduced filtrate to obtain a safflower dry paste;

providing 100 g of Red Paeony Root decoction pieces; heating and boiling the Red Paeony Root decoction pieces with process water of 10 times the weight of the Red Paeony Root decoction pieces to obtain a first decoction after 2 hours slight boiling; filtering the first decoction to obtain filtrate I and a first dreg; boiling the first dreg with process water of 8 times the weight of the first dreg to obtain a second decoction after 1 hour slight boiling; filtering the second decoction to obtain filtrate II and a second dreg; mixing filtrate I and filtrate II to obtain a mixture; concentrating the mixture to obtain a first concentrate of 100 ml; adding a proper amount of gelatin solution to the first concentrate under stirring to obtain a gelatin-containing first concentrate; adding 95% ethanol to the gelatin-containing first concentrate to obtain an ethanol-containing first concentrate having an ethanol volume content of 70%; storing the ethanol-containing first concentrate under cooling condition for 24 hours to obtain a cool ethanol-containing first concentrate; filtering and concentrating the cool ethanol-containing first concentrate to obtain a second concentrate of 100 ml; extracting the second concentrate with water-saturated n-butanol for 4 times and using 50 ml water-saturated n-butanol for each time; combining extract liquors of the 4 times extraction to obtain a combined extract liquor; recycling n-butanol from the combined extract liquor to obtain a n-butanol-reduced extract liquor without alcohol taste; and vacuum drying the n-butanol-reduced extract liquor to obtain a Red Paeony Root dry paste;

providing 100 g of *Ligusticum wallichii* decoction pieces, 100 g of *Radix salviae miltiorrhizae* and 100 g of *Angelica sinensis* decoction pieces; treating the three decoction pieces with a same treatment process as the Red Paeony Root decoction pieces except for keeping 300 ml of concentrate every time and extracting with 150 ml of water-saturated n-butanol each time, to obtain a third dry paste;

providing the safflower dry paste, the Red Paeony Root dry paste and the third dry paste each of a proper amount; dissolving the three dry pastes in injection water to obtain a dilute of 200 ml; storing the dilute under cooling condition to obtain a first cool liquid; adding glucosum anhydricum of an amount in accordance with 4.5% mass fraction of the multi-component injection and injection water to the first cool liquid to obtain a 1000 ml liquid; adjusting the pH value of the 1000 ml liquid to 5.5-7.0 with a sodium hydroxide solution of 10% mass fraction to obtain a pH adjusted liquid; storing the pH adjusted liquid under cooling condition to obtain a second cool liquid; subjecting the second cool liquid to ultrafiltration to obtain an ultrafiltrate; adding a proper amount of solubilizing auxiliary materials which are dissolved in a proper amount of injection water into the ultrafiltrate to obtain a solubilizing auxiliary materials-containing ultrafiltrate; adjusting the pH value of the solubilizing auxiliary materials-containing ultrafiltrate to 5.5-7.0 using the sodium hydroxide solution of 10% mass fraction to obtain a pH adjusted ultrafiltrate; filtering the pH adjusted ultrafiltrate to obtain a filtrate; encapsulating and sterilizing the filtrate to obtain the multi-component injection.

Any one of multi-component injections of the invention is characterized in that the administration way thereof is injection administration.

Any one of multi-component injections of the invention is used for preparing medicines for treating Sepsis.

As the active ingredients in the multi-component injections of the invention are known substances, which can be acquired via the known methods, the preparation method for the multi-component injections of the invention also comprises the steps: mixing the above active ingredients which are purchased or prepared, and preparing the injection via the conventional technology of pharmaceutics.

The technical solution of the invention patent is further described via the following experiments:

The multi-component injection of the present invention has therapeutic effects on the Sepsis cell model and the Sepsis mouse model, indicating that the multi-component injection of the present invention has therapeutic effects on the Sepsis of mammals, thereby achieving therapeutic effects on the Sepsis of human bodies.

The advantages of the present invention will be further detailed via the following experiment data:

Experiment I Effects of the Multi-Component Injection on the Death of Endotoxin Induced Sepsis Mice Experiment Animals Balb/C male mice (purchased from Laboratory Animal Center of Peking Union Medical College), cleaning level, 6-8 weeks, weight of 19-23 g, adaptive feeding for 3 days.

Medicine and Reagent

The medicines of the invention are prepared in accordance with the embodiments 2-5, and endotoxin is purchased from U.S. Sigma Company.

Experiment Method 3.1 Grouping and Intervention 280 mice are divided into a normal group, a model group, experimental groups 1-12 randomly, and there are 20 mice in each group. The mice are prohibited from being fed for 12 h before the experiment, weighed and subjected to grouping in accordance with the table of random numbers. In the model group, only the modeling of counteracting toxic substances by endotoxin is carried out; in experimental groups 1-12, 12 batches of multi-component injections in embodiments 2-5 are received respectively for medicine intervention with administration by injection (the first batch in the embodiment 2 to the third batch of the embodiment 5 are assigned to the experiment groups 1-12 successively) after the modeling of counteracting toxic substances by endotoxin has been carried out; and the normal group is not subjected to additional intervention. The modeling process of counteracting toxic substances by endotoxin is as below: the mixed solution of ketamine hydrochloride:sumianxin II:PBS (phosphate buffer)=1:1.5:2.5 is selected as anaesthetic, and intramuscular injection is carried out for anesthesia in a dose of 2 mL/kg. After anesthesia is satisfied, the mice are fixed on the operating table, and 10 mg/kg of endotoxin is injected to the enterocoelia of the mice. In experimental groups 1-12, 12 batches of multi-component injections in embodiments 2-5 are injected at the auricular vein with a dose of 4 mL/kg (by weight) at 30 min and 60 min before counteracting toxic substances by endotoxin and 30 min after counteracting toxic substances by endotoxin respectively; in the model group, normal saline are injected at auricular vein with 4 mL/kg (by weight) at 30 min and 60 min before counteracting toxic substances by endotoxin and 30 min after counteracting toxic substances by endotoxin.

3.2 Observation and Statistics of Death Rate

Dead mice are observed and counted every 24 h. Statistic analysis is carried out by Kaplan-Merer method (statistics software is SPSS16.0), and $p<0.05$ indicates significant difference.

Experiment Results

The results indicate that the death rate of the Sepsis model group is 100%, within 7 days after the injection of endotoxin, whereas the death rates of the experimental groups 1-12 are shown as the table below, which are obviously lower than that of the Sepsis model group ($p<0.05$).

The above results prompt that in embodiments 2-5, 12 batches of multi-component injections have the protective effects on Sepsis mice caused by endotoxin.

TABLE 1

The effects of 12 batches of multi-component injections in embodiments 2-5 on the death of Sepsis mice caused by endotoxin.

| Group | Quantity | Death number of the 7th day after being attacked by endotoxin | Death rate (%) |
|---|---|---|---|
| Normal group | 20 | 0 | 0 |
| Model group | 20 | 20 | 100 |
| Experimental group 1 | 20 | 7 | 35* |
| Experimental group 2 | 20 | 8 | 40* |
| Experimental group 3 | 20 | 9 | 45* |
| Experimental group 4 | 20 | 8 | 40* |
| Experimental group 5 | 20 | 8 | 40* |
| Experimental group 6 | 20 | 9 | 45* |
| Experimental group 7 | 20 | 8 | 40* |
| Experimental group 8 | 20 | 8 | 40* |
| Experimental group 9 | 20 | 7 | 35* |
| Experimental group 10 | 20 | 7 | 35* |

TABLE 1-continued

The effects of 12 batches of multi-component injections in embodiments 2-5 on the death of Sepsis mice caused by endotoxin.

| Group | Quantity | Death number of the 7th day after being attacked by endotoxin | Death rate (%) |
|---|---|---|---|
| Experimental group 11 | 20 | 7 | 35* |
| Experimental group 12 | 20 | 7 | 35* |

Note:
*indicates p < 0.05 compared with the model group.

Experiment II Effects of the Multi-Component Injection on the Death of Cecal Ligation and Puncture Mediated Sepsis Mice Experiment Animals Balb/C male mice (purchased from Laboratory Animal Center of Peking Union Medical College), cleaning level, 6-8 weeks, weight of 19-23 g, adaptive feeding for 3 days.

Medicine and Reagent

The medicines of the invention are prepared in accordance with the embodiments 2-5.

Experiment Method 3.1 Grouping and Intervention 280 mice are divided into a control group, a model group, experimental groups 1-12 randomly, and there are 20 mice in each group. The mice are prohibited from being fed for 12 h before the experiment, weighed and subjected to grouping in accordance with the table of random numbers. In the control group, only the same operation process is carried out, but neither ligation nor puncture is carried out on caecum; in the model group, the cecal ligation and puncture (CLP) is carried out; for experimental groups 1-12, 12 batches of multi-component injections in embodiments 2-5 are injected respectively (the first batch in the embodiment 2 to the third batch of the embodiment 5 are administered to the experimental groups 1-12 successively) for medicine intervention after CLP modeling. The CLP modeling process is as below: the mixed solution of ketamine hydrochloride:sumianxin II:PBS=1:1.5:2.5 is selected as anaesthetic, and intramuscular injection is carried out for anesthesia at a dose of 2 mL/kg. After anesthesia is satisfied, the mice are fixed on the operating table, thorax and abdomen of the mice are subjected to conventional disinfection for draping, the median abdominal incision is carried out at a position 1 cm below the xiphoid, with an incision length of 1.5 cm. The cecum is exposed and is subjected to ligation at ½ position, and a 21G syringe needle penetrates through ligated cecum and avoids blood vessels. After it is confirmed that there is no active bleeding, the cecum is returned to the enterocoelia, and the incision of abdominal wall is sutured. The postoperation skin behind the neck is subjected to conventional disinfection, 1 mL normal saline is subcutaneous injected for anabiosis, and after coming round from anesthesia, each of the mice is raised in a single cage. After the mice are subjected to the CLP operation, 12 batches of multi-component injections in embodiments 2-5 are respectively injected from the auricular vein in the experimental groups 1-12, at 0.5 h, 12 h, 24 h, 36 h, 48 h, 60 h, 72 h, 84 h and 96 h after the operation, with dosage of 4 mL/kg; and in the model group and the control group, 4 mL/kg (by weight) of normal saline is injected from the auricular vein at corresponding time.

3.2 Observation and Statistics of Death Rate

Dead mice are observed and counted every 24 h. Statistic analysis is carried out via the Kaplan-Merer method (statistics software is SPSS16.0), and p<0.05 indicates significant difference.

Experiment Results

The results indicate that the death rate of the Sepsis model group is 70%, within 7 days after CLP operation, whereas the death rates of the experimental groups 1-12 are shown as the table below. Where, the death rates of the experimental groups 7-12 are obviously lower than that of the Sepsis model group (p<0.05). It indicates that in the embodiment 4 (experiment groups 7-9) and embodiment 5 (experiment groups 10-12), a plurality of batches of multi-component injections have the protective effects on the Sepsis mice caused by endotoxin.

TABLE 2

The effects of 12 batches of multi-component injections in embodiments 2-5 on the death of CLP mediated Sepsis mice.

| Group | Quantity | Death number of the 7th day after CLP operation | Death rate (%) |
|---|---|---|---|
| Control group | 20 | 0 | 0 |
| Model group | 20 | 14 | 70 |
| Experimental group 1 | 20 | 10 | 50 |
| Experimental group 2 | 20 | 11 | 55 |
| Experimental group 3 | 20 | 10 | 50 |
| Experimental group 4 | 20 | 8 | 40 |
| Experimental group 5 | 20 | 8 | 40 |
| Experimental group 6 | 20 | 8 | 40 |
| Experimental group 7 | 20 | 5 | 25* |
| Experimental group 8 | 20 | 6 | 30* |
| Experimental group 9 | 20 | 6 | 30* |
| Experimental group 10 | 20 | 5 | 25* |
| Experimental group 11 | 20 | 5 | 25* |
| Experimental group 12 | 20 | 5 | 25* |

Note:
*indicates P < 0.05 compared with the Sepsis model group.

Experiment III the Effects of the Multi-Component Injection on the Expression of High-Mobility Family Protein B1 of Sepsis Rats Experiment Animals Wistar male rats (purchased from Experimental Animal Research Institute of Chinese Academy of Medical Sciences), cleaning level, weight of 180-220 g, adaptive feeding for 1 week.

Medicine and Reagent

The medicines of the present invention are prepared in accordance with the embodiments 2-5; the kit for high-mobility family protein B1 (HMGB1) enzyme linked immunosorbent assay (ELISA) (Japanese Shino-Test Company).

Experiment Method 3.1 Grouping and Intervention 140 rats are divided into a control group, a model group, experimental groups 1-12 randomly, and there are 10 rats in each group. The rats are prohibited from being fed for 12 h before the experiment, weighed and subjected to grouping in accordance with the table of random numbers. In the control group, laparotomy is carried out to expose the cecum, the skin is sutured, and then, 10 ml of normal saline is subcutaneous injected for anabiosis; in the Sepsis model group, the cecal ligation and puncture (CLP) is carried out for modeling; and in experimental groups 1-12, 12 batches of multi-component injections in embodiments 2-5 are injected respectively (the first batch in the embodiment 2 to the third batch of the embodiment 5 are administered to the experiment groups 1-12 successively) for medicine intervention after CLP modeling. In the CLP modeling processes, the mixed solution of ketamine injection+sumianxin II injection of 2:1 is subjected to intramuscular injection to anesthetize rats, and the Sepsis animal model is prepared using CLP. At the joint of the ligated cecum and the ileum, the No. 18 syringe needle penetrates through the cecum for 2 times to form intestinal fistula, 2 drainage strips (0.5 cm×2.0 cm) are indwelled to prevent needle hole from healing, then, skin is sutured layer by layer, and 10 mL of normal saline is immediately subcutaneously injected for anabiosis after the operation. After the rats are subjected to the CLP operation, in the experiment groups 1-12, at 2 h, 12 h, 24 h, 36 h, 48 h and 60 h, after the operation, 12 batches of multi-component injections in embodiments 2-5 are respectively injected from the dorsal vein of penis, with a dose of 4 mL/kg; and in the model group and the control group, 4 mL/kg (by weight) of normal saline is injected from the dorsal vein of penis at the corresponding time.

3.2 Blood Sampling and Testing

Animals of each group, which are anesthetized, are subjected to sterile blood sampling with 3 mL at abdominal aorta at 2 h, 8 h, 24 h, 48 h and 72 h after CLP, and plasma HMGB1 content is detected via the enzyme linked immunosorbent assay (ELISA).

Experiment Results

The results indicate that in the control group, plasma contains a little amount of HMGB1; in the early stage after the CLP operation, HMGB1 content in the model group is obviously increased, the HMGB1 level at 8 h is further improved, and is gradually reduced after 24 h, but is still higher than that of the control group at 72 h after the operation. There is statistical significance between the two groups ($p<0.05$). While in the experiment groups 1-12 with intervention treatment via 12 batches of multi-component injection in embodiments 2-5, the plasma content at 2 h after the operation is obviously lower than that of the model group ($p<0.05$), HMGB1 is reduced more obviously ($p<0.01$) after 24 h, which is close to the level of the control group. The results prompt that 12 batches of multi-component injections in embodiments 2-5 have the inhibiting effects on the expression of HMGB1 during Sepsis.

Medicine and Reagent

The medicines of the invention are prepared in accordance with the embodiments 2-5; the kit for tissue factor (TF) enzyme linked immunosorbent assay (ELISA) (USA USCN Company); fluorescein isothiocyanate (FITC) labelled anti-rat monocyte protease activated receptor-1 (PAR-1) antibody (USA Santa Cruz Company).

Experiment Method 3.1 Grouping and Intervention 140 rats are divided into a control group, a model group, experimental groups 1-12 randomly, and there are 10 rats in each group. The rats are prohibited from being fed for 12 h before the experiment, weighed and subjected to grouping in accordance with the table of random numbers. In the control group, laparotomy is carried out to expose the cecum, after that, the skin is sutured, and then, 10 mL of normal saline is injected subcutaneously for anabiosis; in the Sepsis model group, the cecal ligation and puncture (CLP) is carried out for modeling; and in experiment groups 1-12, 12 batches of multi-component injections in embodiments 2-5 are injected respectively (the first batch in the embodiment 2 to the third batch of the embodiment 5 are administered to the experiment groups 1-12 successively) for medicine intervention after CLP modeling. In the CLP modeling processs, the mixed solution of ketamine injection:sumianxin II injection=2:1 is used to intramuscular injection to anesthetize rats, and the Sepsis animal model is prepared using CLP. At the joint of the ligated cecum and the ileum, the No. 18 syringe needle penetrates through the cecum for 2 times to form intestinal fistula, 2 drainage strips (0.5 cm×2.0 cm) are indwelled to prevent needle hole from healing, then, skin is sutured layer by layer, and 10 mL of normal saline is immediately subcutaneously injected for anabiosis after the operation. After the rats are subjected to the CLP operation, in the experimental groups 1-12, 12 batches of multi-

TABLE 3

The effects of 12 batches of multi-component injections in embodiments 2-5 on the HMGB1 level of Sepsis rat plasma ($\bar{x} \pm s$, n = 10) Unit: μg/L

| Group | 2 h after operation | 8 h after operation | 24 h after operation | 48 h after operation | 72 h after operation |
|---|---|---|---|---|---|
| Control group | 8.2 ± 2.8 | 8. 3 ± 2.5 | 8. 0 ± 2.3 | 8. 1 ± 1.6 | 8.2 ± 2.2 |
| Model group | 28.8 ± 10.8# | 31.7 ± 7.2# | 23.2 ± 6.3# | 15.3 ± 1.3# | 17.3 ± 1.1# |
| Experimental group 1 | 15.3 ± 5.2* | 17.4 ± 3.3* | 8.2 ± 1.7* | 8.0 ± 2.2* | 8.1 ± 1.3* |
| Experimental group 2 | 17. 2 ± 5.7* | 19.2 ± 7.8* | 8.4 ± 2.0* | 6.8 ± 1.5* | 10. 5 ± 1.4* |
| Experimental group 3 | 17. 0 ± 5.3* | 19. 5 ± 6.1* | 9.0 ± 2.7* | 7.1 ± 2.2* | 10.7 ± 2.5* |
| Experimental group 4 | 16.3 ± 5.5* | 19.0 ± 3.9* | 8.4 ± 2.7* | 7.9 ± 2.0* | 8.9 ± 1.8* |
| Experimental group 5 | 15.9 ± 5.4* | 19.4 ± 3.9* | 8.5 ± 2.4* | 7.2 ± 1.9* | 10.1 ± 1.4* |
| Experimental group 6 | 17.0 ± 5.5* | 18.7 ± 3.9* | 8.5 ± 1.7* | 7.9 ± 1.9* | 10.4 ± 1.9* |
| Experimental group 7 | 15.3 ± 5.6* | 19.2 ± 5.6* | 9.0 ± 2.2* | 6.9 ± 2.0* | 10.4 ± 1.7* |
| Experimental group 8 | 17.0 ± 5.3* | 18.0 ± 6.6* | 8.9 ± 2.4* | 7.4 ± 2.0* | 8.3 ± 1.6* |
| Experimental group 9 | 17.2 ± 5.6* | 18.9 ± 7.5* | 8.8 ± 2.6* | 7.7 ± 2.0* | 9.4 ± 2.5* |
| Experimental group 10 | 16.4 ± 5.3* | 19.2 ± 5.4* | 8.9 ± 2.5* | 7.6 ± 1.5* | 9.6 ± 1.6* |
| Experimental group 11 | 16.3 ± 5.3* | 18.5 ± 6.0* | 8.4 ± 2.5* | 7.7 ± 2.1* | 9.7 ± 1.4* |
| Experimental group 12 | 16.2 ± 5.5* | 17.6 ± 6.4* | 8.5 ± 2.5* | 7.4 ± 1.5* | 10.1 ± 2.4* |

Note:
indicates that $p < 0.05$ compared with the control group;
*indicates $p < 0.05$ compared with the model group.

Experiment IV the Effects of the Multi-Component Injection on the Expression of Monocyte Protease Activated Receptor-1 and Tissue Factors of Sepsis Rats Experiment Animals Wistar male rats (purchased from Experimental Animal Research Institute of Chinese Academy of Medical Sciences), cleaning level, weight of 180-220 g, adaptive feeding for 1 week.

component injections in embodiments 2-5 are respectively injected from the dorsal vein of penis, with a dose of 4 mL/kg at 2 h, 12 h, 24 h, 36 h, 48 h and 60 h, after the operation; and in the model group and the control group, 4 mL/kg (by weight) of normal saline is injected from the dorsal vein of penis at the corresponding time.

3.2 Blood Sampling and Testing

Animals of each group, which are anesthetized, are subjected to sterile blood sampling with 3 mL at aorta abdominalis at 12 h, 24 h, 48 h, 48 h and 72 h after CLP. The expression of the plasma monocyte protease activated receptor-1 (PAR-1) is detected by using the flow immumofluorescence method; and the content of plasma tissue factors (TF) are detected by using the enzyme linked immunosorbent assay (ELISA).

Detection of PAR-1 expression: taking 2 mL of heparin for anticoagulant, and separating mono karyocyte by using rat lymphocyte separating medium; resuspendeding mono karyocyte by using 10% of the full cell culture fluid of fetal calf serum-RPMI 1640, adjusting cell density to be 4×106/mL, and washing a cell culture plate using the cell culture fluid after incubating for 2 h; adding 0.25% trypsin-EDTA digestive juice for digesting 3 min, after majority of cells exfoliating, adding 2 mL of full cell culture fluid of 10% fetal calf serum-RPMI 1640, and terminating digesting; washing using phosphate buffer (PBS) for 3 times to acquire peripheral blood mononuclear cells; adding 1 μg/1×106 cell fluorescein isothiocyanate (FITC) into cell suspension to mark the anti-rat PAR-1 antibody, incubating away from light at 4° C. for 15 min, adding 2 mL of PBS to wash for 1 time, adding 0.4 mL of PBS, and detecting its average fluorescence intensity on the flow cytometry.

Experiment Results

The results indicate that the mononuclear cells PAR-1 in the control group have a certain expression; there is no statistical significance for difference of the expression quantity of PAR-1 at 12 h after the operation between the model group and the control group upon comparison, the average fluorescence intensity is significantly higher than that of the control group at 24 h, 48 h and 72 h after the operation (p<0.05), and gradually increased with the extension of postoperation time. The average fluorescence intensities of PAR-1 at 24 h and 48 h in the experiment groups 1-3 are lower than that of the model group, with no significant difference; and the fluorescence intensities of the experiment groups at 72 h are significantly lower than that of the model group (p<0.05). The average fluorescence intensities of PAR-1 of nine intervention groups of the experiment groups 4-12 at 24 h, 48 h and 72 h are significantly reduced (p<0.05) by comparison to that of the model group.

The mononuclear cells TF in the control group have a certain expression; the expression of TF at 12 h, 24 h, 48 h and 72 h after the operation in the model group are significantly higher than that of the control group (p<0.05), which is gradually increased with the extension of postoperation time, and reach a peak at 48 h. The expression of TF at 12 h and 72 h in the experiment groups 1-3 are lower than that of the model group, with no significant difference; and the expression intensities of the experiment groups at 24 h and 48 h are significantly higher than that of the model group (p<0.05). The expression of TF of nine intervention groups of the experiment groups 4-12 at 24 h, 48 h and 72 h are significantly reduced (p<0.05) by comparison to that of the model group.

The results indicate that the 9 batches of multi-component injections in embodiments 3-5 can reduce the expression of Sepsis induced monocyte PAR-1, thereby obviously reducing the secretion of TF, and improving the monocyte mediated coagulation dysfunction.

TABLE 4-1

The effects of multi-component injections on the expression of Sepsis rats PAR-1 ($\bar{x} \pm s$, n = 10)

| Group | 12 h after operation | 24 h after operation | 48 h after operation | 72 h after operation |
| --- | --- | --- | --- | --- |
| Control group | 20.0 ± 0.7 | 17.6 ± 2.0 | 15.7 ± 0.2 | 16.8 ± 2.9 |
| Model group | 19.8 ± 1.1 | 21.9 ± 1.1# | 24.2 ± 0.7# | 29.7 ± 0.4# |
| Experimental group 1 | 19.6 ± 1.9 | 20.2 ± 2.3 | 22.9 ± 2.0 | 22.6 ± 2.3* |
| Experimental group 2 | 20.8 ± 2.1 | 20.4 ± 1.7 | 23.1 ± 1.8 | 21.6 ± 2.2* |
| Experimental group 3 | 20.7 ± 3.3 | 20.9 ± 1.6 | 22.7 ± 2.7 | 22.8 ± 1.5* |
| Experimental group 4 | 20.0 ± 3.2 | 18.6 ± 1.7* | 20.7 ± 2.2* | 18.0 ± 2.1* |
| Experimental group 5 | 20.2 ± 2.9 | 18.8 ± 1.7* | 18.6 ± 2.6* | 18.3 ± 1.7* |
| Experimental group 6 | 20.3 ± 2.3 | 19.2 ± 1.8* | 18.3 ± 2.5* | 18.1 ± 2.2* |
| Experimental group 7 | 20.2 ± 2.7 | 19.1 ± 1.9* | 20.6 ± 2.0* | 17.9 ± 2.1* |
| Experimental group 8 | 20.7 ± 2.2 | 18.7 ± 1.7* | 21.4 ± 2.3* | 17.9 ± 1.5* |
| Experimental group 9 | 20.0 ± 2.5 | 18.4 ± 2.0* | 18.7 ± 2.1* | 17.7 ± 1.7* |
| Experimental group 10 | 19.9 ± 2.4 | 18.4 ± 1.6* | 18.0 ± 2.2* | 17.9 ± 2.3* |
| Experimental group 11 | 20.3 ± 2.5 | 18.7 ± 1.9* | 21.5 ± 2.1* | 17.8 ± 2.1* |
| Experimental group 12 | 20.7 ± 2.6 | 18.5 ± 2.3* | 18.1 ± 1.9* | 17.7 ± 2.2* |

Note:
indicates that p < 0.05 compared with the control group;
*indicates p < 0.05 compared with the model group.

TABLE 4-2

The effects of multi-component injections on the expression of TF of Sepsis rats ($\bar{x} \pm s$, n = 10) Unit: ng/L

| Groups | 12 h after operation | 24 h after operation | 48 h after operation | 72 h after operation |
| --- | --- | --- | --- | --- |
| Control group | 238.3 ± 15.6 | 221.8 ± 40.7 | 259.0 ± 27.57 | 240.5 ± 34.4 |
| Model group | 324.0 ± 18.9# | 505.2 ± 82.8# | 695.4 ± 138.9# | 342.9 ± 36.3# |
| Experimental group 1 | 299.3 ± 29.6 | 370.0 ± 22.3* | 377.8 ± 26.1* | 319.7 ± 28.3 |
| Experimental group 2 | 296.4 ± 32.3 | 366.7 ± 19.3* | 380.7 ± 41.3* | 313.9 ± 25.3 |
| Experimental group 3 | 297.7 ± 33.3 | 374.3 ± 21.3* | 381.0 ± 19.7* | 320.0 ± 31.2 |

TABLE 4-2-continued

The effects of multi-component injections on the expression of TF of
Sepsis rats ($\bar{x} \pm s$, n = 10) Unit: ng/L

| Groups | 12 h after operation | 24 h after operation | 48 h after operation | 72 h after operation |
|---|---|---|---|---|
| Experimental group 4 | 283.5 ± 24.6* | 273.2 ± 20.8* | 281.4 ± 39.2* | 252.5 ± 23.8* |
| Experimental group 5 | 285.3 ± 29.1* | 273.7 ± 21.4* | 282.6 ± 31.3* | 255.8 ± 19.4* |
| Experimental group 6 | 279.7 ± 26.5* | 268.6 ± 21.1* | 284.9 ± 39.6* | 257.1 ± 20.0* |
| Experimental group 7 | 283.3 ± 31.9* | 270.5 ± 20.7* | 284.0 ± 20.0* | 251.7 ± 25.4* |
| Experimental group 8 | 284.2 ± 30.7* | 273.0 ± 21.2* | 280.2 ± 31.5* | 254.8 ± 29.7* |
| Experimental group 9 | 281.9 ± 29.7* | 273.4 ± 20.8* | 280.5 ± 40.0* | 252.1 ± 25.2* |
| Experimental group 10 | 284.5 ± 23.9* | 271.1 ± 19.5* | 281.8 ± 30.3* | 250.8 ± 26.3* |
| Experimental group 11 | 283.9 ± 31.2* | 270.1 ± 19.9* | 286.1 ± 21.4* | 250.1 ± 27.5* |
| Experimental group 12 | 282.7 ± 20.3* | 268.5 ± 19.9* | 283.7 ± 39.4* | 252.8 ± 19.8* |

Note:
indicates that $p < 0.05$ compared with the control group;
*indicates $p < 0.05$ compared with the model group.

Experiment V the Effects of the Multi-Component Injection on Regulating T Cell Apoptosis and T Helper Cell Drift of Sepsis Rats Experiment Animals Wistar male rats (purchased from Experimental Animal Research Institute of Chinese Academy of Medical Sciences), cleaning level, weight of 180-220 g, adaptive feeding for 1 week.

Medicine and Reagent

The medicines of the invention are prepared in accordance with the embodiments 2-5; phycoerythrin (PE)-anti-rat CD25, fluorescein isothiocyanate (FITC) labeled anti-rat CD4, allophycocyanin (APC) labeled Annexin V apoptosis reagent kit (USA BD Company); rat anti-PE reagent kit, CD4 magnetic beads, MiniMACS magnetic separation apparatus and separation column (Germany MiltenyiBiotec Company); PE labeled forkhead winged helix transcription factor (Foxp3) reagent kit, PE labeled T lymphocytotoxicity related antigen 4 (CTLA-4), anti-rat CD3 monoclonal antibody, anti-rat CD28 monoclonal antibody (USA eBioscience Company); interferon (IFN)-7, IL-4, IL-10 enzyme linked immunosorbent assay (ELISA) reagent kits (USA Biosource Company); IL-17 ELISA reagent kit (USA Usenlife Science Company); Trypan Blue (USA Sigma Company).

Experiment Method 3.1 Grouping and Intervention 140 rats are divided into a control group, a model group, experimental groups 1-12 randomly, and there are 10 rats in each group. The rats are prohibited from being fed for 12 h before the experiment, weighed and subjected to grouping in accordance with the table of random numbers. In the control group, laparotomy is carried out to expose the cecum, after that, the skin is sutured, and then, 10 mL of normal saline is injected subcutaneously for anabiosis; in the Sepsis model group, the cecal ligation and puncture (CLP) is carried out for modeling; and in experiment groups 1-12, 12 batches of multi-component injections in embodiments 2-5 are injected respectively (the first batch in the embodiment 2 to the third batch of the embodiment 5 are administered to the experiment groups 1-12 successively) for medicine intervention after CLP modeling. In the CLP modeling processs, the mixed solution of ketamine injection:sumianxin II injection of 2:1 is intramuscular injected to anesthetize rats, and the Sepsis animal model is prepared by using CLP. At the joint of the ligated cecum and the ileum, the No. 18 syringe needle penetrates through the cecum for 2 times to form intestinal fistula, 2 drainage strips (0.5 cm×2.0 cm) are indwelled to prevent needle hole from healing, then, skin is sutured layer by layer, and 10 mL of normal saline is immediately injected subcutaneously for anabiosis after the operation. After the rats are subjected to the CLP operation, in the experiment groups 1-12, after the operation, 12 batches of multi-component injections in embodiments 2-5 are respectively injected from the dorsal vein of penis, with a dose of 4 mL/kg; and in the model group and the control group, 4 mL/kg (by weight) of normal saline is injected from the dorsal vein of penis at the corresponding time.

3.2 Cell Separation and Culture

Take spleen from each group of rats after breaking necks to death under the sterile condition, grinding the spleen, sieve it with a 400-mesh sieve, centrifuge cell suspension, add lymphocyte separating medium for centrifuging, and obtain white cells in the middle layer. Add PE-anti-CD25 and PE magnetic beads, carry out positive selection (positive) to obtain CD25+T cells, and carry out negative selection (negative) to obtain CD25-T cell. After carrying out dissociation by CD25+T cell dissociation reagent, carry out positive selection on negatively selected cells using FITC-anti-CD4 and CD4 magnetic beads to obtain CD4+CD25+Treg; and carry out positive selection on CD25-T cells using FITC-anti-CD4 and CD4 magnetic beads to obtain CD4+CD25-T cells. Test the purity of double positive cells via the flow cytometry. Dye CD4+CD25+Treg using 0.4% (mass fraction) of Trypan Blue, and observe cell survival rate. Put RPMl1640 culture solution containing 20% (volume fraction) fetal bovine serum in a 48-pore culture plate, and culture in a $CO_2$ incubator. Separate CD4+CD25+Treg in each group at the 3rd day for culturing for 12 h, adjust the concentration of CD4+CD25+Treg and CD4+CD25-T cells by using the culture solution to be 1:1 for culturing, stimulate using sword bean A (Con A, 5 mg/L), culture in a $CO_2$ incubator at 37° C. for 68 h, centrifuge to get a supernate which is frozen at −70° C. for testing.

3.3 Detection and Analysis

Testing of Treg apoptosis rate: culturing the separated cells for 12 h, washing the suspending CD4+CD25+Treg ($1\times10^9$/L) 2 times with phosphate buffer (PBS), adding 100 μL of binding buffer and 10 μL of APC labeled Annexin V (20 mg/L), keeping in the dark place at room temperature for 30 min, then, adding 10 μL of actinomycin D (7-AAD), keeping in the dark place for reaction for 5 min, adding 400 μL of binding buffer, selecting 7-AAD negative Annexin V positive cells as apoptotic cells by the flow cytometry, and testing the cell apoptosis rate.

Testing of Foxp3 and CTLA-4 expression: Adding 1 ml of newly prepared film-breaking liquid into 100 μL prepared CD4+CD25+Treg (1×109/L), keeping in the dark place at 4° C. for incubating for 2 h, and washing with 2 mL of film-breaking buffer; adding PE-anti-Foxp3, incubating in the dark place at 4° C. for 30 min, washing with 2 mL of film-breaking buffer, centrifuging and discarding supernate, adding 0.5 mL of PBS, and testing the average fluorescence intensity of Foxp3 by the flow cytometry. Directly adding PE-CTLA-4 into the resuspended cells (1×109/L), keeping in the dark place at 4° C. for incubating for 30 min, and testing the average fluorescence intensity of CTLA-4.

Testing of cell factors: including main inhibitory cell factor IL-10 secreted by Treg, IFN-γ secreted by Th1, and IL-4 secreted by Th2. The IL-10 specimen is from supernate collected after the separated Treg is cultured for 12 h in each group, IFN-γ and IL-4 specimens are from supernate collected after CD4+CD25+Treg and CD4+CD25−T cells are subjected to co-culture for 68 h. Tests are performed by using the ELISA reagent kit in accordance with the specification, the standard curve and the regression equation are calculated respectively, the absorbency of the samples is substituted into the standard curve, and the protein concentration of cell factors in the samples are calculated.

Experiment Results

The results indicate that the apoptosis rate of Treg in the model group is obviously lower than that of the control group (p<0.05), the apoptosis rates of the experimental groups 4-12 are significantly higher than that of the model group (p<0.05), and the trends of the experimental groups 1-3 are close, without significant difference. The expression of Foxp3 and CTLA-4 in the model group is obviously higher than that of the control group (p<0.05), the expression of the experimental groups 4-12 are significantly lower than that of the model group (p<0.05), and the trends of the experimental groups 1-3 are close, without significant difference. The secretion level of IL-10 in the model group is obviously higher than that of the control group (p<0.05), the secretion level of the experimental groups 4-12 are significantly lower than that of the model group (p<0.05), and the trends of the experimental groups 1-3 are close, without significant difference. The levels of IFN-γ and IL-4 in the model group are substantially increased compared with the control group, and the levels of IFN-γ and IL-4 in the experimental groups 4-12 are further increased. Compared with the model group, there are statistical significance for difference (p<0.05). The trends of experimental groups 1-3 are close, without significant difference.

The results indicate that 9 batches of multi-component injections in embodiments 3-5 can promote the apoptosis of Sepsis Treg and improve the secretion of cell factors of Treg and effector T cells, and are conducive to correcting the inhibitory state of cellular immunity of organisms.

TABLE 5-1

The effects of 12 batches of multi-component injections in embodiments 2-5 on the apoptosis rate of Treg and the expression of Foxp3 and CTLA-4 of Sepsis rats ($\bar{x} \pm s$, n = 10) Unit: %

| Group | Apoptosis rate | Foxp3 | CTLA |
|---|---|---|---|
| Control group | 9.48 ± 2.2 | 126.5 ± 12.2 | 119.1 ± 6.4 |
| Model group | 5.9 ± 1.5# | 175.0 ± 19.6# | 172.0 ± 10.1# |
| Experimental group 1 | 7.1 ± 3.0 | 159.8 ± 13.3 | 159.7 ± 14.1 |
| Experimental group 2 | 7.3 ± 2.5 | 159.7 ± 16.8 | 161.4 ± 19.9 |
| Experimental group 3 | 7.0 ± 2.3 | 158.5 ± 15.1 | 160.0 ± 20.7 |
| Experimental group 4 | 17.4 ± 2.5* | 118.9 ± 14.4* | 118.3 ± 15.2* |
| Experimental group 5 | 17.9 ± 3.0* | 118.8 ± 14.1* | 116.2 ± 18.3* |
| Experimental group 6 | 17.9 ± 2.9* | 119.6 ± 14.1* | 116.4 ± 15.6* |
| Experimental group 7 | 28.0 ± 2.9* | 59.7 ± 4.2* | 55.5 ± 6.5* |
| Experimental group 8 | 27.3 ± 2.4* | 58.9 ± 5.5* | 55.6 ± 6.3* |
| Experimental group 9 | 27.4 ± 2.8* | 58.6 ± 6.3* | 56.3 ± 6.6* |
| Experimental group 10 | 27.9 ± 2.9* | 59.0 ± 3.5* | 58.6 ± 5.8* |
| Experimental group 11 | 27.8 ± 2.5* | 59.5 ± 5.8* | 56.5 ± 7.4* |
| Experimental group 12 | 27.2 ± 3.0* | 59.5 ± 3.3* | 56.8 ± 4.2* |

Note:
indicates that p < 0.05 compared with the control group;
*indicates p < 0.05 compared with the model group.

TABLE 5-2

The effects of 12 batches of multi-component injections in embodiments 2-5 on the level of secretory cell factors of Treg and effector T cells of Sepsis rats ($\bar{x} \pm s$, n = 10) Unit: ng/L

| Group | IL-10 | IFN-γ | IL-4 |
|---|---|---|---|
| Control group | 133.7 ± 25.7 | 19.0 ± 6.7 | 5.4 ± 0.7 |
| Model group | 318.1 ± 28.3# | 254.7 ± 44.9# | 8.8 ± 0.6# |
| Experimental group 1 | 299.3 ± 22.3 | 311.6 ± 75.2 | 9.3 ± 0.9 |
| Experimental group 2 | 300.6 ± 22.1 | 321.5 ± 84.3 | 9.5 ± 1.2 |
| Experimental group 3 | 302.6 ± 22.5 | 322.8 ± 88.9 | 9.3 ± 1.1 |
| Experimental group 4 | 245.2 ± 22.5* | 414.7 ± 82.2* | 10.4 ± 0.8* |
| Experimental group 5 | 251.5 ± 22.2* | 413.2 ± 78.2* | 10.3 ± 1.0* |
| Experimental group 6 | 251.6 ± 19.3* | 408.8 ± 84.1* | 10.5 ± 1.3* |
| Experimental group 7 | 51.2 ± 2.5* | 498.7 ± 81.7* | 10.5 ± 1.2* |
| Experimental group 8 | 49.6 ± 2.2* | 494.2 ± 85.3* | 10.7 ± 1.1* |
| Experimental group 9 | 52.2 ± 2.3* | 495.6 ± 81.9* | 10.6 ± 0.9* |
| Experimental group 10 | 50.3 ± 2.1* | 499.4 ± 85.6* | 10.8 ± 1.4* |
| Experimental group 11 | 49.3 ± 2.3* | 501.4 ± 87.6* | 10.7 ± 1.1* |
| Experimental group 12 | 51.7 ± 2.1* | 494.5 ± 81.0* | 10.8 ± 1.3* |

Note:
indicates that p < 0.05 compared with the control group;
*indicates p < 0.05 compared with the model group.

After related testing, we find that the multi-component injections of the present invention have the characteristics of stable quality, simple production process, convenience for production, safety, effectiveness, etc.

The summary of relevant compounds presented in the present application:

| Name | CAS | Molecular formula | Structural formula |
|---|---|---|---|
| Kaempferol-3-0-glucoside | 480-10-4 | $C_{21}H_{20}O_{11}$ | |
| Scutellarin | 27740-01-8 | $C_{21}H_{18}O_{12}$ | |
| Quercetin-3-0-glucoside | 482-35-9 | $C_{21}H_{20}O_{12}$ | |
| Kaempferol-3-0-rutinoside | 17650-84-9 | $C_{27}H_{30}O_{15}$ | |

-continued

| Name | CAS | Molecular formula | Structural formula |
|---|---|---|---|
| Kaempferol-3-0-sophoroside | 19895-95-5 | $C_{27}H_{30}O_{16}$ | |
| Quercetin-3-0-rutinoside | 949926-49-2 | $C_{27}H_{30}O_{16}$ | |
| Hydroxysafflor yellowA | 78281-02-4 | $C_{27}H_{32}O_{16}$ | |
| Uracil | 66-22-8 | $C_4H_4N_2O_2$ | |
| Adenine | 73-24-5 | $C_5H_5N_5$ | |

-continued

| Name | CAS | Molecular formula | Structural formula |
|---|---|---|---|
| Phenylalanine | 167088-01-9 | $C_9H_{11}NO_2$ | |
| Uridine | 58-96-8 | $C_9H_{12}N_2O_6$ | |
| Adenosine | 58-61-7 | $C_{10}H_{13}N_5O_4$ | |
| Guanosine | 118-00-3 | $C_{10}H_{13}N_5O_5$ | |
| Butanedioic acid | 110-15-6 | $C_4H_6O_4$ | |
| p-hydroxybenzoic acid | 99-96-7 | $C_7H_6O_3$ | |
| p-coumaric acid | 501-98-4 | $C_9H_8O_3$ | |
| Caffeic acid | 331-39-5 | $C_9H_8O_4$ | |

-continued

| Name | CAS | Molecular formula | Structural formula |
|---|---|---|---|
| Chlorogenic acid | 327-97-9 | $C_{16}H_{18}O_9$ | |
| Albiflorin std | 39011-90-0 | $C_{23}H_{28}O_{11}$ | |
| Paeoniflorin | 23180-57-6 | $C_{23}H_{28}O_{11}$ | |
| Oxypaeoniflorin | 39011-91-1 | $C_{23}H_{28}O_{12}$ | |
| Benzoylpaeoniflorin | 38642-49-8 | $C_{30}H_{32}O_{12}$ | |

-continued

| Name | CAS | Molecular formula | Structural formula |
|---|---|---|---|
| Benzoyloxy paeoniflorin | 72896-40-3 | $C_{30}H_{32}O_{13}$ | |
| Mudanpioside J | 262350-52-7 | $C_{31}H_{34}O_{14}$ | |
| Galloylpaeoniflorin | 122965-41-7 | $C_{30}H_{32}O_{15}$ | |

-continued

| Name | CAS | Molecular formula | Structural formula |
|---|---|---|---|
| Mudanpioside C | 172760-03-1 | $C_{30}H_{32}O_{13}$ | |
| Benzoic acid | 65-85-0 | $C_7H_6O_2$ | |
| Gallic acid | 149-91-7 | $C_7H_6O_5$ | |
| Ethyl gallate | 831-61-8 | $C_9H_{10}O_5$ | |
| Catechin | 154-23-4 | $C_{15}H_{14}O_6$ | |
| Protocatechualdehyde | 139-85-5 | $C_7H_6O_3$ | |
| Protocatechuic acid | 99-50-3 | $C_7H_6O_4$ | |

-continued

| Name | CAS | Molecular formula | Structural formula |
|---|---|---|---|
| Tanshinol | 76822-21-4 | $C_9H_{10}O_5$ | |
| Rosmarinic acid | 537-15-5 | $C_{18}H_{16}O_8$ | |
| Salvianolic acid D | 142998-47-8 | $C_{20}H_{18}O_{10}$ | |
| Salvianolic acid C | 115841-09-3 | $C_{26}H_{20}O_{10}$ | |
| Salvianolic acid A | 96574-01-5 | $C_{26}H_{22}O_{10}$ | |

-continued

| Name | CAS | Molecular formula | Structural formula |
| --- | --- | --- | --- |
| Alkannic acid | 28831-65-4 | $C_{27}H_{22}O_{12}$ | |
| Salvianolic acid B | 121521-90-2 | $C_{36}H_{30}O_{16}$ | |
| Senkyunolide I | 94596-28-8 | $C_{12}H_{16}O_4$ | |
| Senkyunolide H | 94596-27-7 | $C_{12}H_{16}O_4$ | |
| Senkyunolide N | 140694-58-2 | $C_{12}H_{18}O_4$ | |
| Open-loop senkyunolide I | 1809299-03-3 | $C_{12}H_{18}O_5$ | |

-continued

| Name | CAS | Molecular formula | Structural formula |
|---|---|---|---|
| Senkyunolide G | 94530-85-5 | $C_{12}H_{16}O_3$ | |
| 3-hydroxy-3-Butylphthalide | 162050-42-2 | $C_{12}H_{14}O_3$ | |
| Senkyunolide A | 62006-39-7 | $C_{12}H_{16}O_2$ | |
| Ferulaic acid | 1135-24-6 | $C_{10}H_{10}O_4$ | |

IV. DESCRIPTION OF THE DRAWINGS

FIG. 1 Comparison of survival rates of endotoxin induced Sepsis mice among groups Note: compared with the model group, the experimental groups 1-12 have the significant statistical difference ($p<0.05$).

Figure 2:
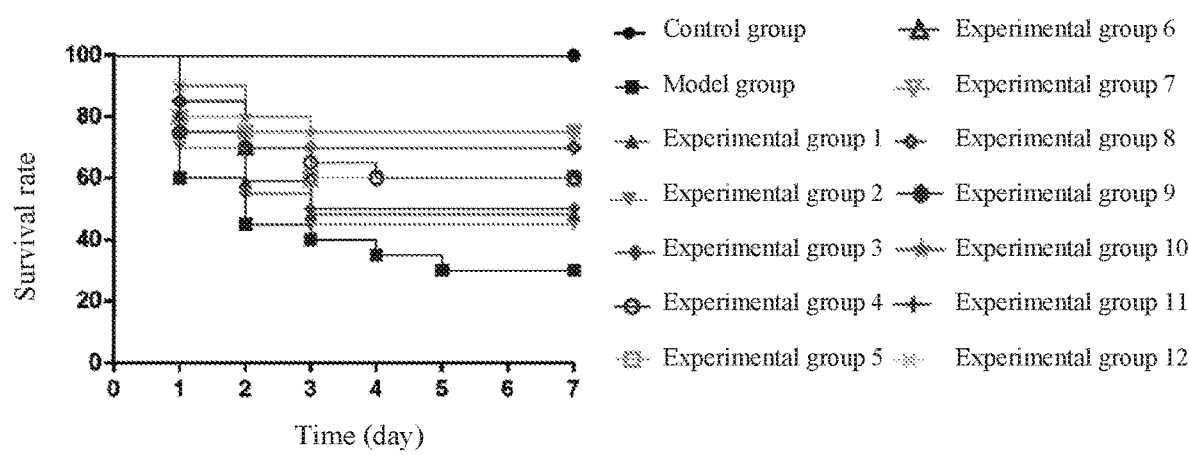

FIG. 2 Comparison of the survival rates of cecal ligation and puncture mediated Sepsis mice among groups Note: compared with the model group, the experimental groups 7-12 have the significant statistical difference ($p<0.05$).

V. DETAILED DESCRIPTION OF THE EMBODIMENTS

There is a further description to the invention via the following specific embodiments, which is not used as limits.

Embodiment 1 Testing Method for Effective Ingredients in Injection

Method 1: Chromatographic Separation Conditions for Analyzing Ingredients of Safflower (*Carthamus tinctorius*) and Red Paeony Root
  Chromatographic column: Waters HSS T3 UPLC C18 Chromatographic column (100 mm×2.1 mm; 1.8 μM, Waters, USA);
  Column temperature: 45° C.;
  Mobile phase: A: $H_2O$ (containing 25 mM HCOOH, B: MeOH (containing 25 mM HCOOH);
  Gradient elute is shown in Table 6; flow velocity: 0.35 mL/min; injection volume: 5 μL; analysis time: 13 min.

TABLE 6

Liquid-phase gradient elute conditions of ingredients of safflower carthamus and Red Paeony Root

| Time (min) | Solvent A | Solvent B |
|---|---|---|
| 0.0 | 98% | 2% |
| 8.0 | 30% | 70% |
| 11.0 | 2% | 98% |
| 13.0 | 98% | 2% |

Method 2: Chromatographic Separation Conditions for Analyzing Ingredients of *Radix salviae miltiorrhizae*
  Chromatographic column: Waters HSS T3 UPLC C18 Chromatographic column (100 mm×2.1 mm; 1.8 μM, Waters, USA);
  Column temperature: 45° C.;
  Mobile phase: A: $H_2O$ (containing 25 mM HCOOH), B: MeOH (containing 25 mM HCOOH);
  Gradient elute is shown in Table 7; flow velocity: 0.35 mL/min; injection volume: 5 μL; analysis time: 20 min.

TABLE 7

Liquid-phase gradient elute conditions of ingredients of radix salviae miltiorrhizae

| Time (min) | Solvent A | Solvent B |
|---|---|---|
| 0.0 | 98% | 2% |
| 1.0 | 98% | 2% |
| 15.0 | 30% | 70% |
| 17.0 | 2% | 98% |
| 20.0 | 98% | 2% |

Method 3: Chromatographic Separation Conditions for Analyzing Ingredients of *Ligusticum wallichii* and *Angelica sinensis*, Adenine and Adenosine Chromatographic column: Waters HSS T3 UPLC C18 Chromatographic column (100 mm×2.1 mm; 1.8 µM, Waters, USA);

Column temperature: 45° C.;

Mobile phase: A: MeOH—H$_2$O (v/v, 1:99), including 1 mM HCOOH and 25 µM, CH3COOLi; B: MeOH—H$_2$O (v/v, 99:1), including 1 mM HCOOH and 25 µM, CH3COOLi;

Gradient elute is shown in Table 8; flow velocity: 0.35 mL/min; injection volume: 5 µL; analysis time: 8 min.

TABLE 8

Liquid-phase gradient elute conditions of ingredients of Ligusticum wallichii and Angelica sinensis, adenine and adenosine

| Time (min) | Solvent A | Solvent B |
| --- | --- | --- |
| 0.0 | 94% | 6% |
| 7.0 | 5% | 95% |
| 8.0 | 94% | 6% |

Embodiment 2 Preparation of Multi-Component Injection providing 100 g of Red Paeony Root decoction pieces; heating and boiling the Red Paeony Root decoction pieces with process water of 10 times the weight of the Red Paeony Root decoction pieces to obtain a first decoction after 2 hours slight boiling; filtering the first decoction to obtain filtrate I and a first dreg; boiling the first dreg with process water of 8 times the weight of the first dreg to obtain a second decoction after 1 hour slight boiling; filtering the second decoction to obtain filtrate II and a second dreg; mixing filtrate I and filtrate II to obtain a mixture; concentrating the mixture to obtain a first concentrate of 100 ml; adding a proper amount of gelatin solution to the first concentrate under stirring to obtain a gelatin-containing first concentrate; adding 95% ethanol to the gelatin-containing first concentrate to obtain an ethanol-containing first concentrate having an ethanol volume content of 70%; storing the ethanol-containing first concentrate under cooling condition for 24 hours to obtain a cool ethanol-containing first concentrate; filtering and concentrating the cool ethanol-containing first concentrate to obtain a second concentrate of 100 ml; extracting the second concentrate with water-saturated n-butanol for 4 times and using water-saturated n-butanol of 50 ml for each time; combining extract liquors of the 4 times extraction to obtain a combined extract liquor; recycling n-butanol from the combined extract liquor to obtain a n-butanol-reduced extract liquor without alcohol taste; and vacuum drying the n-butanol-reduced extract liquor to obtain a Red Paeony Root dry paste;

providing a proper amount of the Red Paeony Root dry paste; dissolving the Red Paeony Root dry paste in injection water to obtain a dilute of 200 ml; storing the dilute under cooling condition to obtain a first cool liquid; adding glucosum anhydricum of an amount in accordance with 4.5% mass fraction of the multi-component injection and injection water to the first cool liquid to obtain a 1000 ml liquid; adjusting the pH value of the 1000 ml liquid to 5.5-7.0 with a sodium hydroxide solution of 10% mass fraction to obtain a pH adjusted liquid; storing the pH adjusted liquid under cooling condition to obtain a second cool liquid; subjecting the second cool liquid to ultrafiltration to obtain an ultrafiltrate; adding a proper amount of solubilizing auxiliary materials which are dissolved in a proper amount of injection water into the ultrafiltrate to obtain a solubilizing auxiliary materials-containing ultrafiltrate; adjusting the pH value of the solubilizing auxiliary materials-containing ultrafiltrate to 5.5-7.0 using the sodium hydroxide solution of 10% mass fraction to obtain a pH adjusted ultrafiltrate; filtering the pH adjusted ultrafiltrate to obtain a filtrate; encapsulating and sterilizing the filtrate to obtain the multi-component injection.

Three batches of injections are prepared in accordance with the process, and the testing results of the effective ingredients are as below:

| Effective ingredient (Unit ug/ml) | The First batch | The Second batch | The Third batch |
| --- | --- | --- | --- |
| Albiflorin std | 8.66 | 9.51 | 11.98 |
| Paeoniflorin | 1000.0 | 1010.7 | 1051.6 |
| Oxypaeoniflorin | 11.13 | 14.43 | 14.45 |
| Benzoylpaeoniflorin | 12.20 | 15.48 | 18.09 |
| Benzoyloxypaeoniflorin | 0.667 | 0.711 | 0.753 |
| Mudanpioside J | 1.915 | 1.934 | 1.960 |
| Galloylpaeoniflorin | 10.63 | 11.03 | 11.15 |
| Mudanpioside C | 0.804 | 0.805 | 0.941 |
| Benzoic acid | 10.0 | 20.4 | 30.1 |
| Gallic acid | 0.21 | 0.73 | 0.77 |
| Ethyl gallate | 0.2396 | 0.2428 | 0.2526 |
| Catechin | 1.31 | 1.91 | 1.60 |

Embodiment 3 Preparation Process of Multi-Component Injection providing 100 g of safflower (*Carthamus tinctorius*) decoction pieces; leaching the safflower decoction pieces with 30% ethanol of 8 times the weight of the safflower decoction pieces for 8 hours to obtain a leach liquor; filtering the leach liquor to obtain a liquid medicine of 4-6 times the weight of the safflower decoction pieces; adding 95% ethanol to the liquid medicine to obtain an ethanol-containing liquid medicine having an ethanol volume content of 70%; storing the ethanol-containing liquid medicine under cooling condition for 48 hours to obtain a cool ethanol-containing liquid medicine; filtering the cool ethanol-containing liquid medicine to obtain a first filtrate; concentrating the first filtrate under reduced pressure to obtain a concentrate of 100 ml; adding 95% ethanol to the concentrate to obtain an ethanol-containing concentrate having an ethanol volume content of 80%; storing the ethanol-containing concentrate under cooling condition for 48 hours to obtain a cool ethanol-containing concentrate; filtering the cool ethanol-containing concentrate to obtain a second filtrate; recycling ethanol from the second filtrate to obtain an ethanol-reduced filtrate; concentrating and vacuum drying the ethanol-reduced filtrate to obtain a safflower dry paste;

providing 100 g of Red Paeony Root decoction pieces; heating and boiling the Red Paeony Root decoction pieces with process water of 10 times the weight of the Red Paeony Root decoction pieces to obtain a first decoction after 2 hours slight boiling; filtering the first decoction to obtain filtrate I and a first dreg; boiling the first dreg with process water of 8 times the weight of the first dreg to obtain a second decoction after 1 hour slight boiling; filtering the second decoction to obtain filtrate II and a second dreg; mixing filtrate I and filtrate II to obtain a mixture; concentrating the mixture to obtain a first concentrate of 100 ml; adding a proper amount of gelatin solution to the first concentrate under stirring to obtain a gelatin-containing first concentrate; adding 95% ethanol to the gelatin-containing first concentrate to obtain an ethanol-containing first concentrate having an ethanol volume content of 70%; storing the ethanol-containing first concentrate under cooling condition for 24 hours to obtain a cool ethanol-containing first concentrate; filtering and concentrating the cool ethanol-containing first concentrate to obtain a second concentrate of 100 ml; extracting the second concentrate with water-saturated n-butanol for 4 times and using 50 ml water-saturated n-butanol for each time; combining extract liquors of the 4 times extraction to obtain a combined extract liquor; recycling n-butanol from the combined extract liquor to obtain a n-butanol-reduced extract liquor without alcohol taste; and vacuum drying the n-butanol-reduced extract liquor to obtain a Red Paeony Root dry paste;

providing the safflower dry paste and the Red Paeony Root dry paste each of a proper amount; dissolving the two dry pastes in injection water to obtain a dilute of 200 ml; storing the dilute under cooling condition to obtain a first cool liquid; adding glucosum anhydricum of an amount in accordance with 4.5% mass fraction of the multi-component injection and injection water to the first cool liquid to obtain a 1000 ml liquid; adjusting the pH value of the 1000 ml liquid to 5.5-7.0 with a sodium hydroxide solution of 10% mass fraction to obtain a pH adjusted liquid; storing the pH adjusted liquid under cooling condition to obtain a second cool liquid; subjecting the second cool liquid to ultrafiltration to obtain an ultrafiltrate; adding a proper amount of solubilizing auxiliary materials which are dissolved in a proper amount of injection water into the ultrafiltrate to obtain a solubilizing auxiliary materials-containing ultrafiltrate; adjusting the pH value of the solubilizing auxiliary materials-containing ultrafiltrate to 5.5-7.0 using the sodium hydroxide solution of 10% mass fraction to obtain a pH adjusted ultrafiltrate; filtering the pH adjusted ultrafiltrate to obtain a filtrate; encapsulating and sterilizing the filtrate to obtain the multi-component injection.

Three batches of injections are prepared in accordance with the above process, and the testing results of the effective ingredients are as below:

| Effective ingredient (Unit ug/ml) | The First batch | The Second batch | The Third batch |
|---|---|---|---|
| Albiflorin std | 13.58 | 15.46 | 15.01 |
| Paeoniflorin | 1119.7 | 1139.7 | 1209.5 |
| Oxypaeoniflorin | 21.45 | 24.17 | 24.24 |
| Benzoylpaeoniflorin | 21.20 | 21.55 | 24.19 |
| Benzoyloxypaeoniflorin | 0.820 | 0.844 | 0.904 |
| Mudanpioside J | 2.083 | 2.463 | 2.480 |
| Galloylpaeoniflorin | 11.48 | 11.81 | 13.96 |
| Mudanpioside C | 0.942 | 1.031 | 1.048 |
| Benzoic acid | 84.8 | 85.8 | 100.2 |
| Gallic acid | 6.68 | 5.72 | 8.41 |
| Ethyl gallate | 0.3083 | 0.3967 | 0.4453 |
| Catechin | 4.01 | 5.86 | 5.97 |
| Kaempferol-3-0-glucoside | 1.232 | 1.440 | 1.506 |
| Scutellarin | 0.0500 | 0.0570 | 0.1033 |
| Quercetin-3-0-glucoside | 0.755 | 0.859 | 0.973 |
| Kaempferol-3-0-rutinoside | 8.42 | 11.02 | 12.59 |
| Kaempferol-3-0-sophoroside | 4.036 | 4.369 | 4.954 |
| Quercetin-3-0-rutinoside | 1.517 | 1.529 | 1.774 |
| Hydroxysafflor yellow A | 200.0 | 225.5 | 229.8 |
| Uracil | 0.316 | 0.338 | 0.424 |
| Adenine | 13.77 | 14.31 | 16.45 |
| Phenylalanine | 20.50 | 24.22 | 36.02 |
| Uridine | 11.44 | 13.25 | 14.26 |
| Adenosine | 5.07 | 5.59 | 5.70 |
| Guanosine | 8.00 | 9.06 | 10.02 |
| Butanedioic acid | 4.96 | 5.67 | 8.23 |
| p-hydroxybenzoic acid | 2.384 | 2.997 | 3.040 |
| p-coumaric acid | 3.00 | 3.23 | 3.79 |
| Caffeic acid | 4.837 | 5.298 | 5.584 |
| Chlorogenic acid | 3.83 | 3.86 | 4.28 |

Embodiment 4 Preparation Process of Multi-Component Injection providing 100 g of safflower (*Carthamus tinctorius*) decoction pieces; leaching the safflower decoction pieces with 30% ethanol of 8 times the weight of the safflower decoction pieces for 8 hours to obtain a leach liquor; filtering the leach liquor to obtain a liquid medicine of 4-6 times the weight of the safflower decoction pieces; adding 95% ethanol to the liquid medicine to obtain an ethanol-containing liquid medicine having an ethanol volume content of 70%; storing the ethanol-containing liquid medicine under cooling condition for 48 hours to obtain a cool ethanol-containing liquid medicine; filtering the cool ethanol-containing liquid medicine to obtain a first filtrate; concentrating the first filtrate under reduced pressure to obtain a concentrate of 100 ml; adding 95% ethanol to the concentrate to obtain an ethanol-containing concentrate having an ethanol volume content of 80%; storing the ethanol-containing concentrate under cooling condition for 48 hours to obtain a cool ethanol-containing concentrate; filtering the cool ethanol-containing concentrate to obtain a second filtrate; recycling ethanol from the second filtrate to obtain an ethanol-reduced filtrate; concentrating and vacuum drying the ethanol-reduced filtrate to obtain a safflower dry paste;

providing 100 g of Red Paeony Root decoction pieces; heating and boiling the Red Paeony Root decoction pieces with process water of 10 times the weight of the Red Paeony Root decoction pieces to obtain a first decoction after 2 hours slight boiling; filtering the first decoction to obtain filtrate I and a first dreg; boiling the first dreg with process water of 8 times the weight of the first dreg to obtain a second decoction after 1 hour slight boiling; filtering the second decoction to obtain filtrate II and a second dreg; mixing filtrate I and filtrate II to obtain a mixture; concentrating the mixture to obtain a first concentrate of 100 ml; adding a proper amount of gelatin solution to the first concentrate under stirring to obtain a gelatin-containing first concentrate; adding 95% ethanol to the gelatin-containing first concentrate to obtain an ethanol-containing first concentrate having an ethanol volume content of 70%; storing the ethanol-containing first concentrate under cooling condition for 24 hours to obtain a cool ethanol-containing first concentrate; filtering and concentrating the cool ethanol-containing first concentrate to obtain a second concentrate of 100 ml; extracting the second concentrate with water-saturated n-butanol for 4 times and using 50 ml water-saturated n-butanol for each time; combining extract liquors of the 4 times extraction to obtain a combined extract liquor; recycling n-butanol from the combined extract liquor to obtain a n-butanol-reduced extract liquor without alcohol taste; and vacuum drying the n-butanol-reduced extract liquor to obtain a Red Paeony Root dry paste;

providing 100 g of *Ligusticum wallichii* decoction pieces and 100 g of *Angelica sinensis* decoction pieces; treating the *Ligusticum wallichii* decoction pieces and *Angelica sinensis* decoction pieces with a same treatment process as the Red Paeony Root decoction pieces except for keeping 300 ml of concentrate every time and extracting with 150 ml of water-saturated n-butanol each time, to obtain a third dry paste;

providing the safflower dry paste, the Red Paeony Root dry paste and the third dry paste each of a proper amount; dissolving the three dry pastes in injection water to obtain a dilute of 200 ml; storing the dilute under cooling condition to obtain a first cool liquid; adding glucosum anhydricum of an amount in accordance with 4.5% mass fraction of the multi-component injection and injection water to the first cool liquid to obtain a 1000 ml liquid; adjusting the pH value of the 1000 ml liquid to 5.5-7.0 with a sodium hydroxide solution of 10% mass fraction to obtain a pH adjusted liquid; storing the pH adjusted liquid under cooling condition to obtain a second cool liquid; subjecting the second cool liquid to ultrafiltration to obtain an ultrafiltrate; adding a proper amount of solubilizing auxiliary materials which are dissolved in a proper amount of injection water into the ultrafiltrate to obtain a solubilizing auxiliary materials-containing ultrafiltrate; adjusting the pH value of the solubilizing auxiliary materials-containing ultrafiltrate to 5.5-7.0 using the sodium hydroxide solution of 10% mass fraction to obtain a pH adjusted ultrafiltrate; filtering the pH adjusted ultrafiltrate to obtain a filtrate; encapsulating and sterilizing the filtrate to obtain the multi-component injection.

Three batches of injections are prepared in accordance with the process, and the testing results of the effective ingredients are as below:

| Effective ingredient (Unit ug/ml) | The First batch | The Second batch | The Third batch |
| --- | --- | --- | --- |
| Albiflorin std | 19.06 | 22.10 | 22.27 |
| Paeoniflorin | 1227.3 | 1263.2 | 1286.0 |
| Oxypaeoniflorin | 40.38 | 43.28 | 43.69 |
| Benzoylpaeoniflorin | 32.04 | 34.49 | 35.72 |
| Benzoyloxypaeoniflorin | 1.364 | 1.396 | 1.436 |
| Mudanpioside J | 2.516 | 2.729 | 2.773 |
| Galloylpaeoniflorin | 15.07 | 15.71 | 16.16 |
| Mudanpioside C | 1.060 | 1.074 | 1.170 |
| Benzoic acid | 153.4 | 165.4 | 176.3 |
| Gallic acid | 8.80 | 10.12 | 13.70 |
| Ethyl gallate | 0.5517 | 0.5527 | 0.5863 |
| Catechin | 9.95 | 10.37 | 10.45 |
| Kaempferol-3-0-glucoside | 1.646 | 1.723 | 1.898 |
| Scutellarin | 0.1236 | 0.1307 | 0.1766 |
| Quercetin-3-0-glucoside | 1.482 | 1.775 | 1.918 |
| Kaempferol-3-0-rutinoside | 13.87 | 14.82 | 14.93 |
| Kaempferol-3-0-sophoroside | 5.321 | 5.542 | 5.619 |
| Quercetin-3-0-rutinoside | 2.669 | 2.788 | 3.150 |
| Hydroxysafflor yellow A | 250.4 | 311.5 | 329.9 |
| Uracil | 0.440 | 0.476 | 0.477 |
| Adenine | 16.56 | 17.27 | 19.82 |
| Phenylalanine | 31.17 | 31.85 | 32.93 |
| Uridine | 14.78 | 15.23 | 19.32 |
| Adenosine | 6.66 | 6.72 | 7.24 |
| Guanosine | 10.07 | 10.81 | 11.95 |
| Butanedioic acid | 9.51 | 9.78 | 10.04 |
| p-hydroxybenzoic acid | 3.054 | 3.447 | 3.712 |
| p-coumaric acid | 10.61 | 12.46 | 12.55 |
| Caffeic acid | 5.627 | 5.971 | 6.212 |
| Chlorogenic acid | 4.32 | 4.53 | 4.68 |
| Senkyunolide I | 6.51 | 7.72 | 8.06 |
| Senkyunolide H | 1.55 | 2.93 | 2.51 |
| Senkyunolide N | 4.30 | 4.86 | 6.17 |
| Open-loop senkyunolide I | 2.460 | 3.037 | 3.132 |
| Senkyunolide G | 1.55 | 2.06 | 2.12 |
| 3-hydroxy-3-Butylphthalide | 1.43 | 1.7 | 2.38 |
| Senkyunolide A | 0.10 | 0.183 | 0.203 |
| Ferulaic acid | 7.66 | 8.41 | 10.23 |

Embodiment 5 Preparation Process of Multi-Component Injection providing 100 g of safflower (*Carthamus tinctorius*) decoction pieces; leaching the safflower decoction pieces with 30% ethanol of 8 times the weight of the safflower decoction pieces for 8 hours to obtain a leach liquor; filtering the leach liquor to obtain a liquid medicine of 4-~6 times the weight of the safflower decoction pieces; adding 95% ethanol to the liquid medicine to obtain an ethanol-containing liquid medicine having an ethanol volume content of 70%; storing the ethanol-containing liquid medicine under cooling condition for 48 hours to obtain a cool ethanol-containing liquid medicine; filtering the cool ethanol-containing liquid medicine to obtain a first filtrate; concentrating the first filtrate under reduced pressure to obtain a concentrate of 100 ml; adding 95% ethanol to the concentrate to obtain an ethanol-containing concentrate having an ethanol volume content of 80%; storing the ethanol-containing concentrate under cooling condition for 48 hours to obtain a cool ethanol-containing concentrate; filtering the cool ethanol-containing concentrate to obtain a second filtrate; recycling ethanol from the second filtrate to obtain an ethanol-reduced filtrate; concentrating and vacuum drying the ethanol-reduced filtrate to obtain a safflower dry paste;

providing 100 g of Red Paeony Root decoction pieces; heating and boiling the Red Paeony Root decoction pieces with process water of 10 times the weight of the Red Paeony Root decoction pieces to obtain a first decoction after 2 hours slight boiling; filtering the first decoction to obtain filtrate I and a first dreg; boiling the first dreg with process water of 8 times the weight of the first dreg to obtain a second decoction after 1 hour slight boiling; filtering the second decoction to obtain filtrate II and a second dreg; mixing filtrate I and filtrate II to obtain a mixture; concentrating the mixture to obtain a first concentrate of 100 ml; adding a proper amount of gelatin solution to the first concentrate under stirring to obtain a gelatin-containing first concentrate; adding 95% ethanol to the gelatin-containing first concentrate to obtain an ethanol-containing first concentrate having an ethanol volume content of 70%; storing the ethanol-containing first concentrate under cooling condition for 24 hours to obtain a cool ethanol-containing first concentrate; filtering and concentrating the cool ethanol-containing first concentrate to obtain a second concentrate of 100 ml; extracting the second concentrate with water-saturated n-butanol for 4 times and using 50 ml water-saturated n-butanol for each time; combining extract liquors of the 4 times extraction to obtain a combined extract liquor; recycling n-butanol from the combined extract liquor to obtain a n-butanol-reduced extract liquor without alcohol taste; and vacuum drying the n-butanol-reduced extract liquor to obtain a Red Paeony Root dry paste;

providing 100 g of *Ligusticum wallichii* decoction pieces, 100 g of *Radix salviae miltiorrhizae* and 100 g of *Angelica sinensis* decoction pieces; treating the three decoction pieces with a same treatment process as the Red Paeony Root decoction pieces except for keeping 300 ml of concentrate every time and extracting with 150 ml of water-saturated n-butanol each time, to obtain a third dry paste; providing the safflower dry paste, the Red Paeony Root dry paste and the third dry paste each of a proper amount; dissolving the three dry pastes in injection water to obtain a dilute of 200 ml; storing the dilute under cooling condition to obtain a first cool liquid; adding glucosum anhydricum of an amount in accordance with 4.5% mass fraction of the multi-component injection and injection water to the first cool liquid to obtain a 1000 ml liquid; adjusting the pH value of the 1000 ml liquid to 5.5-7.0 with a sodium hydroxide solution of 10% mass fraction to obtain a pH adjusted liquid; storing the pH adjusted liquid under cooling condition to obtain a second cool liquid; subjecting the second cool liquid to ultrafiltration to obtain an ultrafiltrate; adding a proper amount of solubilizing auxiliary materials which are dissolved in a proper amount of injection water into the ultrafiltrate to obtain a solubilizing auxiliary materials-containing ultrafiltrate; adjusting the pH value of the solubilizing auxiliary materials-containing ultrafiltrate to 5.5-7.0 using the sodium hydroxide solution of 10% mass fraction to obtain a pH adjusted ultrafiltrate; filtering the pH adjusted ultrafiltrate to obtain a filtrate; encapsulating and sterilizing the filtrate to obtain the multi-component injection.

Three batches of injections are prepared in accordance with the process, and the testing results of the effective ingredients are as below:

| Effective ingredient (Unit ug/ml) | The First batch | The Second batch | The Third batch |
| --- | --- | --- | --- |
| Albiflorin std | 34.94 | 32.30 | 35.26 |
| Paeoniflorin | 1588.2 | 1677.0 | 1700.0 |
| Oxypaeoniflorin | 59.42 | 64.52 | 68.07 |
| Benzoylpaeoniflorin | 47.98 | 48.27 | 52.98 |
| Benzoyloxypaeoniflorin | 1.452 | 1.551 | 1.617 |
| Mudanpioside J | 2.775 | 3.030 | 3.202 |
| Galloylpaeoniflorin | 18.37 | 19.71 | 20.13 |
| Mudanpioside C | 1.225 | 1.277 | 1.338 |
| Benzoic acid | 186.2 | 191.9 | 200.0 |
| Gallic acid | 13.85 | 15.40 | 15.88 |
| Ethyl gallate | 0.6277 | 0.6633 | 0.6860 |
| Catechin | 11.48 | 11.94 | 12.60 |
| Kaempferol-3-0-glucoside | 2.859 | 3.328 | 3.547 |
| Scutellarin | 0.2824 | 0.3620 | 0.4184 |
| Quercetin-3-0-glucoside | 2.295 | 2.263 | 2.570 |

-continued

| Effective ingredient (Unit ug/ml) | The First batch | The Second batch | The Third batch |
| --- | --- | --- | --- |
| Kaempferol-3-0-rutinoside | 22.90 | 26.66 | 29.40 |
| Kaempferol-3-0-sophoroside | 7.384 | 7.667 | 7.695 |
| Quercetin-3-0-rutinoside | 4.420 | 5.288 | 5.598 |
| Hydroxysafflor yellow A | 422.4 | 476.9 | 500.0 |
| Uracil | 0.723 | 0.758 | 0.774 |
| Adenine | 24.44 | 28.49 | 30.56 |
| Phenylalanine | 38.44 | 40.78 | 44.99 |
| Uridine | 23.22 | 26.86 | 27.13 |
| Adenosine | 10.34 | 12.28 | 12.63 |
| Guanosine | 20.68 | 22.95 | 24.11 |
| Butanedioic acid | 15.29 | 15.44 | 16.86 |
| p-hydroxybenzoic acid | 4.690 | 5.363 | 5.404 |
| p-coumaric acid | 15.63 | 17.92 | 17.98 |
| Caffeic acid | 6.909 | 7.774 | 7.806 |
| Chlorogenic acid | 7.74 | 8.48 | 8.59 |
| Senkyunolide I | 60.32 | 63.21 | 69.39 |
| Senkyunolide H | 15.76 | 17.29 | 18.27 |
| Senkyunolide N | 13.36 | 14.18 | 14.22 |
| Open-loop senkyunolide I | 5.126 | 5.190 | 5.648 |
| Senkyunolide G | 10.31 | 10.68 | 10.74 |
| 3-hydroxy-3-Butylphthalide | 7.02 | 7.08 | 8.67 |
| Senkyunolide A | 0.656 | 0.938 | 0.961 |
| Ferulaic acid | 35.62 | 42.68 | 47.15 |
| Protocatechualdehyde | 1.435 | 8.511 | 17.25 |
| Protocatechuic acid | 2.361 | 2.469 | 4.030 |
| Tanshinol | 2.776 | 4.150 | 6.845 |
| Rosmarinic acid | 5.07 | 9.57 | 12.78 |
| Salvianolic acid D | 0.0697 | 0.2892 | 0.4005 |
| Salvianolic acid C | 1.123 | 2.185 | 4.732 |
| Salvianolic acid A | 0.366 | 1.508 | 2.505 |
| Alkannic acid | 0.429 | 0.480 | 0.945 |
| Salvianolic acid B | 4.00 | 8.96 | 11.00 |

The invention claimed is:

1. A method for treating sepsis in a subject in need thereof comprising administering to the subject a multi-component injection, wherein the multi-component injection comprises albiflorin std, paeoniflorin, Oxypaeoniflorin, Benzoylpaeoniflorin, Benzoyloxypaeoniflorin, Mudanpioside J, galloylpaeoniflorin, Mudanpioside C, benzoic acid, gallic acid, ethyl gallate, catechin, Kaempferol-3-0-glucoside, scutellarin, quercetin-3-0-glucoside, Kaempferol-3-0-rutinoside, Kaempferol-3-0-sophoroside, quercetin-3-0-rutinoside, Hydroxysafflor yellow A, uracil, adenine, phenylalanine, uridine, adenosine, guanosine, butanedioic acid, p-hydroxybenzoic acid, p-coumaric acid, caffeic acid, chlorogenic acid, senkyunolide I (42), senkyunolide H, senkyunolide N, open-loop senkyunolide I, senkyunolide G, 3-hydroxyl-3-butylphthalide, senkyunolide A, and ferulaic acid.

2. The method according to claim 1, wherein the multi-component injection comprises 8.66-35.26 parts of albiflorin std, 1000.0-1700.0 parts of paeoniflorin, 11.13-68.07 parts of Oxypaeoniflorin, 12.20-52.98 parts of Benzoylpaeoniflorin, 0.667-1.617 parts of Benzoyloxypaeoniflorin, 1.915-3.202 parts of Mudanpioside J, 10.63-20.13 parts of galloylpaeoniflorin, 0.804-1.338 parts of Mudanpioside C, 10.0-200.0 parts of benzoic acid, 0.21-15.88 parts of gallic acid, 0.2396-0.6860 parts of ethyl gallate, 1.31-12.60 parts of catechin, 1.232-3.547 parts of Kaempferol-3-0-glucoside, 0.0500-0.4184 parts of scutellarin, 0.755-2.570 parts of quercetin-3-0-glucoside, 8.42-29.40 parts of Kaempferol-3-0-rutinoside, 4.036-7.695 parts of Kaempferol-3-0-sophoroside, 1.517-5.598 parts of quercetin-3-0-rutinoside, 200.0-500.0 parts of Hydroxysafflor yellow A, 0.316-0.774 parts of uracil, 13.77-30.56 parts of adenine, 20.50-44.99 parts of phenylalanine, 11.44-27.13 parts of uridine, 5.07-12.63 parts of adenosine, 8.00-24.11 parts of guanosine, 4.96-16.86 parts of butanedioic acid, 2.384-5.404 parts of p-hydroxybenzoic acid, 3.00-17.98 parts of p-coumaric acid, 4.837-7.806 parts of caffeic acid, 3.83-8.59 parts of chlorogenic acid, 6.51-69.39 parts of senkyunolide I (42), 1.55-18.27 parts of senkyunolide H, 4.30-14.22 parts of senkyunolide N, 2.460-5.648 parts of open-loop senkyunolide I, 1.55-10.74 parts of senkyunolide G, 1.43-8.67 parts of 3-hydroxyl-3-butylphthalide, 0.10-0.961 parts of senkyunolide A, and 7.66-47.15 parts of ferulaic acid.

3. The method according to claim 1, wherein the multi-component injection is obtained from safflower (*Carthamus tinctorius*), Red Paeony Root, *Ligusticum wallichii*, and *Angelica sinensis*.

4. The method according to claim 3, the multi-component injection is obtained from equal amounts in weight of safflower (*Carthamus tinctorius*), Red Paeony Root, *Ligusticum wallichii*, and *Angelica sinensis*.

5. The method according to claim 4, wherein the multi-component injection is prepared by a method comprising providing 100 g of safflower (*Carthamus tinctorius*) decoction pieces; leaching the safflower (*Carthamus tinctorius*) decoction pieces for 8 hours to obtain a leach liquor with 30% ethanol, wherein the 30% ethanol is in an amount of 8 times the weight of the safflower (*Carthamus tinctorius*) decoction pieces; filtering the leach liquor to obtain a liquid medicine of 4-6 times the weight of the safflower (*Carthamus tinctorius*) decoction pieces; adding 95% ethanol to the liquid medicine to obtain an ethanol-containing liquid medicine having an ethanol volume content of 70%; storing the ethanol-containing liquid medicine under cooling conditions for 48 hours to obtain a cool ethanol-containing liquid medicine; filtering the cool ethanol-containing liquid medicine to obtain a first filtrate; concentrating the first filtrate under reduced pressure to obtain a concentrate of 100 ml; adding 95% ethanol to the concentrate to obtain an ethanol-containing concentrate having an ethanol volume content of 80%; storing the ethanol-containing concentrate under cooling conditions for 48 hours to obtain a cool ethanol-containing concentrate; filtering the cool ethanol-containing concentrate to obtain a second filtrate; recycling ethanol from the second filtrate to obtain an ethanol-reduced filtrate; concentrating and vacuum drying the ethanol-reduced filtrate to obtain a safflower (*Carthamus tinctorius*) dry paste;

providing 100 g of Red Paeony Root decoction pieces; heating and boiling the Red Paeony Root decoction pieces with water to obtain a first decoction after 2 hours of slight boiling, wherein the water is in an amount of 10 times the weight of the Red Paeony Root decoction pieces; filtering the first decoction to obtain filtrate I and a first dreg; boiling the first dreg with water of 8 times the weight of the first dreg to obtain a second decoction after 1 hour of slight boiling; filtering the second decoction to obtain filtrate II and a second dreg; mixing filtrate I and filtrate II to obtain a mixture; concentrating the mixture to obtain a first concentrate of 100 ml; adding a gelatin solution to the first concentrate under stirring to obtain a gelatin-containing first concentrate; adding 95% ethanol to the gelatin-containing first concentrate to obtain an ethanol-containing first concentrate having an ethanol volume content of 70%; storing the ethanol-containing first concentrate under cooling conditions for 24 hours to obtain a cool ethanol-containing first concentrate; filtering and concentrating the cool ethanol-containing first concentrate to obtain a second concentrate of 100 ml; extracting the second concentrate with water-saturated n-butanol for 4 times and using 50 ml water-saturated n-butanol for each time; combining extract liquors of the 4 times extraction to obtain a combined extract liquor; recycling n-butanol from the combined extract liquor to obtain a n-butanol-reduced extract liquor without alcohol taste; and vacuum drying the n-butanol-reduced extract liquor to obtain a Red Paeony Root dry paste;

providing 100 g of *Ligusticum wallichii* decoction pieces and 100 g of *Angelica sinensis* decoction pieces; treating the *Ligusticum wallichii* decoction pieces and *Angelica sinensis* decoction pieces with a same treatment process as the Red Paeony Root decoction pieces except for keeping 300 ml of a second concentrate instead of 100 mL every time and extracting with 150 ml of water-saturated n-butanol each time, to obtain a third dry paste;

providing the safflower (*Carthamus tinctorius*) dry paste, the Red Paeony Root dry paste and the third dry paste; dissolving the three dry pastes in injection water to obtain a dilute of 200 ml; storing the dilute under cooling conditions to obtain a first cool liquid; adding glucosum anhydricum in an amount that is 4.5% of the weight of the multi-component injection and adding injection water to the first cool liquid to obtain a 1000 ml liquid; adjusting the pH value of the 1000 ml liquid to 5.5-7.0 with a sodium hydroxide solution of 10% mass fraction to obtain a pH adjusted liquid; storing the pH adjusted liquid under cooling conditions to obtain a second cool liquid; subjecting the second cool liquid to ultrafiltration to obtain an ultrafiltrate; adding solubilizing auxiliary materials, which are dissolved in injection water into the ultrafiltrate to obtain a solubilizing auxiliary materials-containing ultrafiltrate; adjusting the pH value of the solubilizing auxiliary materials-containing ultrafiltrate to 5.5-7.0 using the sodium hydroxide solution of 10% mass fraction to obtain a pH adjusted ultrafiltrate; filtering the pH adjusted ultrafiltrate to obtain a filtrate; encapsulating and sterilizing the filtrate to obtain the multi-component injection.

6. The method according to claim 1, wherein the multi-component injection further comprises a solubilizing auxiliary material.

7. The method according to claim 6, wherein the multi-component injection has a pH value of 5.5-7.0.

8. The method according to claim 7, wherein the multi-component injection is suitable for administration via an intramuscular injection, a subcutaneous injection, or an intravenous injection.

9. The method according to claim 2, wherein the multi-component injection further comprises a solubilizing auxiliary material.

10. The method according to claim 9, wherein the multi-component injection has a pH value of 5.5-7.0.

11. The method according to claim 10, wherein the multi-component injection is suitable for administration via an intramuscular injection, a subcutaneous injection, or an intravenous injection.

* * * * *